(12) United States Patent
Kawase et al.

(10) Patent No.: US 7,776,194 B2
(45) Date of Patent: Aug. 17, 2010

(54) GAS CONCENTRATION MEASURING APPARATUS DESIGNED TO COMPENSATE FOR OUTPUT ERROR

(75) Inventors: Tomoo Kawase, Aichi-ken (JP); Eiichi Kurokawa, Okazaki (JP); Koji Jono, Kariya (JP)

(73) Assignee: Denso Corporation, Kariya (JP)

( * ) Notice: Subject to any disclaimer, the term of this patent is extended or adjusted under 35 U.S.C. 154(b) by 1493 days.

(21) Appl. No.: 11/098,500

(22) Filed: Apr. 5, 2005

(65) Prior Publication Data

US 2005/0230248 A1 Oct. 20, 2005

(30) Foreign Application Priority Data

Apr. 16, 2004 (JP) .............................. 2004-122175
Sep. 1, 2004 (JP) .............................. 2004-254786
Sep. 1, 2004 (JP) .............................. 2004-254787

(51) Int. Cl.
*G01N 27/26* (2006.01)

(52) U.S. Cl. ..................... 204/424; 204/425; 205/783.5; 205/784.5; 73/23.31; 73/23.32

(58) Field of Classification Search ......... 204/424–429; 205/783.5–785; 73/23.31–23.32

See application file for complete search history.

(56) References Cited

U.S. PATENT DOCUMENTS

| | | | | |
|---|---|---|---|---|
| 4,532,013 A * | 7/1985 | Dietz et al. | ................... | 205/784 |
| 4,796,587 A | 1/1989 | Nakajima et al. | ............ | 123/440 |
| 4,905,652 A * | 3/1990 | Nakajima et al. | ............ | 123/679 |
| 4,915,813 A | 4/1990 | Nakajima et al. | | |
| 4,981,125 A * | 1/1991 | Kato et al. | ................... | 123/693 |
| 5,925,088 A | 7/1999 | Nasu | ........................... | 701/103 |
| 6,164,125 A | 12/2000 | Kawase et al. | ............. | 73/118.1 |
| 2001/0052473 A1 * | 12/2001 | Ohkuma | ..................... | 205/784 |
| 2003/0080003 A1 * | 5/2003 | Akhavan et al. | ......... | 205/784.5 |

FOREIGN PATENT DOCUMENTS

| | | | |
|---|---|---|---|
| JP | 58-198752 A | 11/1983 |
| JP | 61-294350 A | 12/1986 |
| JP | 2-12055 A | 1/1990 |
| JP | 2-17705 | 4/1990 |
| JP | 7-27391 | 6/1995 |
| JP | 09-274006 | 10/1997 |
| JP | 11-6815 | 1/1999 |

(Continued)

OTHER PUBLICATIONS

Japanese Office Action issued Feb. 5, 2007 in corresponding Japanese Application No. 2004-254787, together with an English translation.

(Continued)

*Primary Examiner*—Nam X Nguyen
*Assistant Examiner*—Bach T Dinh
(74) *Attorney, Agent, or Firm*—Nixon & Vanderhye, P.C.

(57) ABSTRACT

A gas concentration measuring apparatus for use in air-fuel ratio control of motor vehicle engines is provided which is designed to select or determine a correction factor for an output of an A/F sensor, as produced through a sensor control circuit, for compensating for errors in circuit characteristics of the A/F sensor and/or the sensor control circuit to ensure the accuracy of measurement in the apparatus.

14 Claims, 22 Drawing Sheets

FOREIGN PATENT DOCUMENTS

| | | |
|---|---|---|
| JP | 11-211693 | 8/1999 |
| JP | 11-344466 | 12/1999 |
| JP | 2001-221095 | 8/2001 |
| JP | 3257319 | 12/2001 |

OTHER PUBLICATIONS

Office Action dated Nov. 24, 2009 issued in corresponding Japanese Application No. 2004-254786 with an at least partial English-language translation thereof.

Office Action dated Jan. 6, 2010 issued in corresponding Japanese Application No. 2004-254787 with an at least partial English-language translation thereof.

Office Action dated Mar. 17, 2010 issued in corresponding Japanese Application No. 2004-254787 with an at least partial English-language translation thereof.

* cited by examiner

| ID NO. | Ref. Resist.($\Omega$) | ID Resist. ($\Omega$) | ID vol. (V) | Lean side Correction factor | Rich side Correction factor |
|---|---|---|---|---|---|
| 1 | 2.67E+03 | 1.18E+02 | 0.2116 | 1.218032 | 1.191860 |
| 2 | 2.67E+03 | 1.87E+02 | 0.3273 | 1.194312 | 1.171429 |
| 3 | 2.67E+03 | 2.61E+02 | 0.4452 | 1.171498 | 1.151685 |
| 4 | 2.67E+03 | ... | ... | ... | ... |
| 5 | 2.67E+03 | ... | ... | ... | ... |
| 6 | 2.67E+03 | ... | ... | ... | ... |
| 7 | 2.67E+03 | ... | ... | ... | ... |
| 8 | 2.67E+03 | ... | ... | ... | ... |
| 9 | 2.67E+03 | ... | ... | ... | ... |
| 10 | 2.67E+03 | ... | ... | ... | ... |
| 11 | 2.67E+03 | ... | ... | ... | ... |
| 12 | 2.67E+03 | 2.67E+03 | 2.5000 | 1 | 1 |
| 13 | 2.67E+03 | 3.48E+03 | 2.8293 | 0.983607 | 0.985577 |
| 14 | 2.67E+03 | 4.32E+03 | 3.0901 | 0.968808 | 0.971564 |
| 15 | 2.67E+03 | 6.81E+03 | 3.5918 | 0.953037 | 0.957944 |
| 16 | 2.67E+03 | ... | ... | ... | ... |
| 17 | 2.67E+03 | ... | ... | ... | ... |
| 18 | 2.67E+03 | ... | ... | ... | ... |
| 19 | 2.67E+03 | ... | ... | ... | ... |
| 20 | 2.67E+03 | ... | ... | ... | ... |
| 21 | 2.67E+03 | ... | ... | ... | ... |
| 22 | 2.67E+03 | ... | ... | ... | ... |
| 23 | 2.67E+03 | ... | ... | ... | ... |

$E : 10^x$   EX. $2.67E+03 = 2.67 \times 10^3$

Fig. 21

GAS CONCENTRATION MEASURING APPARATUS DESIGNED TO COMPENSATE FOR OUTPUT ERROR

CROSS REFERENCE TO RELATED DOCUMENT

The present application claims the benefit of Japanese Patent Application No. 2004-122175 filed on Apr. 16, 2004, Japanese Paten Application No. 2004-254786 filed on Sep. 1, 2004, and Japanese Patent Application No. 2004-254787 filed on Sep. 1, 2004 the disclosures of which are incorporated herein by reference.

BACKGROUND OF THE INVENTION

1. Technical Field of the Invention

The present invention relates generally to a gas concentration measuring apparatus which may be used in measuring the concentration of a preselected component, such as oxygen, of exhaust emissions of automotive engines, and more particularly to such a gas concentration measuring apparatus designed to correct an output of a gas sensor for compensating for an output error arising from individual variability of the apparatus.

2. Background Art

Limiting current air-fuel (A/F) ratio sensors (also called A/F sensors or lambda sensors) are known which measure the concentration of oxygen ($O_2$) contained in exhaust emissions of motor vehicle engines to determine an air-fuel ratio of a mixture supplied to the engine. A typical one of the A/F sensors includes a sensor element made up of a solid electrolyte body and a pair of electrodes affixed to the solid electrolyte body. The measurement of concentration of oxygen is achieved by applying the voltage to the solid electrolyte body through the electrodes to produce a flow of electrical current through the sensor element as a function of the concentration of oxygen and sampling the electrical current to determine the A/F ratio.

Usually, the A/F sensors or sensor control circuits therefore have individual variability in circuit characteristics, which will result in a decrease in accuracy of measuring the A/F ratio. In order to alleviate this problem, U.S. Pat. No. 5,925,088 (Japanese Patent No. 3257319) teaches a system designed to monitor an event that the A/F sensor is in a non-activated state, sample an actual output of the sensor control circuit in such an event, determine an error between the sampled output and a corresponding reference output, and correct an air-fuel ratio conversion map based on the determined error.

The above system, however, requires sampling an output of the sensor control circuit when the A/F sensor is in the non-activated state for compensating for the error of the output, which gives arise to the problem that a chance of finding the error of the output is limited only to a cold start phase of the A/F sensor. When the temperature of the sensor control circuit is increasing, it is, thus, impossible to find the error of the output precisely, which results in a decrease in accuracy of measuring the A/F ratio. Additionally, it is difficult to monitor the event that the A/F sensor is placed in the non-activated state accurately, which may lead to an error in correcting the air-fuel ratio conversion map.

Control systems for modern automotive gasoline engines are highly required to monitor an air-fuel ratio of a mixture around a stoichiometric air-fuel ratio with high accuracy. To this end, there has been proposed to expand a region around the stoichiometric air-fuel ratio for fine detection of the air-fuel ratio of the mixture. This approach has still left room for improvement of compensating for the error of the output.

U.S. Pat. No. 4,796,587 (Japanese Utility Model Second Publication No. 7-27391) teaches a system designed to select a correction factor used in compensating for an error of an output of an oxygen sensor in response to an identification signal indicative of an error inherent between an actual output of the sensor and a corresponding reference output. Usually, when an automotive engine is running at a high speed and a high load in response to an acceleration demand, it will result in an increased temperature of exhaust gas, which may cause parts of an exhaust system such as a catalytic converter, etc. to be overheated. In order to increase an engine output and avoid such overheating to protect the engine, typical engine control systems increase the amount of fuel supplied to the engine. This, however, causes an air-fuel mixture to be enriched excessively, thus resulting in an increase in fuel consumption. In order to address this problem, technologies are being developed to regulate the quantity of fuel to be injected into the engine using an output of the A/F sensor under rich feedback control.

A combination of the air-fuel ratio feedback control to control the air-fuel ratio around the stoichiometric one and in the lean region and the rich feedback control to control the air-fuel ratio in the rich region serve to ensure the stability in bringing the air-fuel ratio to around the stoichiometric one or in the lean region, but encounters a difficulty in attaining a target air-fuel ratio in the rich region for improving the fuel consumption. This is assumed to be due to a difference in output characteristics of the A/F sensor between when the air-fuel ratio is in the lean region and when it is in the rich region.

SUMMARY OF THE INVENTION

It is therefore a principal object of the invention to avoid the disadvantages of the prior art.

It is another object of the invention to provide a gas concentration measuring apparatus designed to ensure compensation for an error inherent in an output of a gas sensor, as produced through a control circuit, for improving the accuracy of measurement in the apparatus.

According to one aspect of the invention, there is provided a gas concentration measuring apparatus which may be employed in determining an air-fuel ratio of an automotive engine for use in air-fuel ratio control. The gas concentration measuring apparatus comprises: (a) a gas concentration sensor which includes a solid electrolyte body to be exposed to an exhaust gas within an exhaust system of an internal combustion engine; (b) a sensor control circuit which works to control an operation of the gas concentration sensor and operate in a gas measuring mode and a reference output mode selectively, in the gas measuring mode, the sensor control circuit applying a voltage to the gas concentration sensor and sampling a resulting flow of electric current through the gas concentration sensor to produce a gas concentration output as a function of a concentration of a given component of the exhaust gas, in the reference output mode, the sensor control circuit being placed in a condition which is equivalent to when the exhaust gas is in a preselected atmosphere and in which a reference output is produced insensitive to the exhaust gas; (c) a switching circuit working to switch a mode of operation of the sensor control circuit from the gas measuring mode to the reference output mode; and (d) a correcting circuit working to sample a value of the reference output as produced by the sensor control circuit being placed in the reference output mode and find an error of the gas concentration output of the sensor control circuit as a function of a difference between the sampled value of the reference output and a corresponding normal reference output as expected to be attained by the sensor control circuit correctly when the exhaust gas is in the preselected atmosphere to determine a correction factor. The correcting circuit corrects the gas concentration output of the sensor control circuit using the correction factor so as to compensate for the error.

With the above arrangements, the data required to attain the correction factor may be acquired by the switching circuit immediately upon switching to the reference output mode. A chance of finding the error of the gas concentration output is, therefore, not limited, unlike the above described conventional system which requires the event that the sensor is in a non-activated state.

In the preferred mode of the invention, the reference output mode is established by placing the sensor control circuit in a virtual stoichiometric air-fuel ratio measuring mode equivalent to an operation mode in which the sensor control circuit produces the gas concentration output when the exhaust gas results from burning of a stoichiometric mixture in the engine. The stoichiometric air-fuel ratio is a chemically correct ratio at which an air-fuel mixture is burned perfectly. The concentration of oxygen in exhaust gas resulting from such burning will be zero (i.e., sensor current=0 mA). Therefore, in the virtual stoichiometric air-fuel ratio measuring mode, the gas concentration output will be produced by a sensor current of 0 mA as the reference output.

The switching circuit may include a switch installed in a current flow line of the sensor control circuit which connects with the gas concentration sensor. The switching circuit works to open the switch to block the flow of the current from the gas concentration sensor to the sensor control circuit, thereby placing the sensor control circuit in the virtual stoichiometric air-fuel ratio measuring mode in which a current of 0 mA is inputted to the sensor control circuit.

The switching circuit may alternatively include a switch connecting between an output of an amplifier and the gas concentration sensor. The switching circuit works to open the switch to block the flow of the current from the gas concentration sensor to the sensor control circuit, thereby placing the sensor control circuit in the virtual stoichiometric air-fuel ratio measuring mode.

The sensor control circuit may alternatively include a current-measuring resistor and a switch. The current-measuring resistor is connected to one of a positive and a negative terminal of the gas concentration sensor so that the electric current resulting from application of the voltage to the gas concentration sensor flows through the current-measuring resistor. The switch is installed in a current flow line of the sensor control circuit leading to the other of the positive and negative terminals of the gas concentration sensor. The switching circuit works to open the switch to place the sensor control circuit in the virtual stoichiometric air-fuel ratio measuring mode.

The switching circuit may work to place the positive and negative terminals of the gas concentration sensor at the same potential to bring the sensor control circuit into the virtual stoichiometric air-fuel ratio measuring mode.

The switching circuit may switch the mode of operation of the sensor control circuit from the gas measuring mode to the reference output mode at a stated time interval.

The switching circuit may switch the mode of operation of the sensor control circuit from the gas measuring mode to the reference output mode when a control system for the internal combustion engine is in a condition not to require the gas concentration output of the sensor control circuit.

The switching circuit may switch the mode of operation of the sensor control circuit from the gas measuring mode to the reference output mode when the sensor control circuit experiences a change in temperature thereof.

The switching circuit may switch the mode of operation of the sensor control circuit from the gas measuring mode to the reference output mode at least immediately after start-up of the engine or when the engine is stopped.

The correcting circuit may determine the correction factor cyclically to update a value of the correction factor. The correcting circuit stores the updated correction factor.

The correcting circuit may store the updated correction factor on a basis of temperature of the sensor control circuit.

The correcting circuit may also work to sample a value of the gas concentration output which is produced by the sensor control circuit placed in the gas measuring mode when the exhaust gas is in a given reference atmosphere that is different from an atmosphere of the exhaust gas equivalent to when the sensor control circuit produces a value of the gas concentration output identical with the reference output. The correcting circuit finds a second error of the gas concentration output of the sensor control circuit as a function a difference between the sampled value of the gas concentration output and a corresponding normal reference output as expected to be attained by the sensor control circuit correctly when the exhaust gas is in the given reference atmosphere. The correcting circuit determines the correction factor using the second error and a first error that is the error, as found as a function of the difference between the sampled value of the reference output and the corresponding normal reference output, and corrects the gas concentration output of the sensor control circuit using the correction factor so as to compensate for the first and second errors.

The given reference atmosphere may be an atmosphere of the exhaust gas resulting from burning of a mixture equivalent to surrounding air.

The gas concentration measuring apparatus may further include a rich/lean decision circuit which works to decide whether the exhaust gas is in a rich state or a lean state. The correcting circuit may work to determine one of a rich side correction factor and a lean side correction factor which matches one of the rich and lean states, as decided by the rich/lean decision circuit, and is required to compensate for the second error. The correcting circuit corrects the gas concentration output of the sensor control circuit using the one of the rich and lean side correction factor.

The switching circuit may alternatively be designed to produce a current output inhibit signal which inhibits the gas concentration sensor from producing the electric current to bring the sensor control circuit into the virtual stoichiometric air-fuel ratio measuring mode.

The sensor control circuit may include an amplifier through which the voltage is applied to the gas concentration sensor in the gas measuring mode. The switching circuit may work to output an off-signal to disenable the amplifier to bring the sensor control circuit into the virtual stoichiometric air-fuel ratio measuring mode.

According to the second aspect of the invention, there is provided a gas concentration measuring apparatus which comprises: (a) a gas concentration sensor which includes a solid electrolyte body to be exposed to an exhaust gas within an exhaust system of an internal combustion engine; (b) a sensor control circuit which works to apply a voltage to the gas concentration sensor and sample a resulting flow of electric current through the gas concentration sensor to produce a gas concentration output as a function of a concentration of a given component of the exhaust gas; and (c) a correcting circuit working to sample a first and a second value of the gas concentration output when the sensor control circuit is placed in a first and a second condition in which the exhaust gas is in a first and a second atmosphere preselected to be different from each other, respectively. The correcting circuit determines a first and a second error as functions of differences between the first value and a corresponding first normal reference value as expected to be attained by the sensor control circuit correctly when the exhaust gas is in the first atmosphere and between the second value and a corresponding second normal reference value as expected to be attained by the sensor control circuit correctly when the exhaust gas is in the second atmosphere to determine a correction factor. The correcting circuit corrects a value of the gas concentration output of the sensor control circuit using the correction factor so as to compensate for the first and second errors.

In the preferred mode of the invention, the first atmosphere may be an atmosphere of the exhaust gas emitted immediately after start-up of the engine or after stop of the engine. The second atmosphere may be an atmosphere of the exhaust gas resulting from burning of a mixture equivalent to surrounding air.

The correcting circuit may determine and store the first and second errors cyclically to update a value of the correction factor.

The correcting circuit may store the first and second errors on a basis of temperature of the sensor control circuit, respectively.

According to the third aspect of the invention, there is provided a gas concentration measuring apparatus which comprises: (a) a gas concentration sensor which includes a solid electrolyte layer and a diffusion resistance layer and works to produce a sensor output as a function of a concentration of a given gas mixture introduced into the gas concentration sensor through the diffusion resistance layer; (b) a rich/lean decision circuit working to decide whether the gas mixture is in a rich state or a lean state; and (c) a correcting circuit working to correct the sensor output of the gas concentration sensor using one of a rich side correction factor and a lean side correction factor which matches one of the rich and lean states, as decided by the rich/lean decision circuit. This eliminates a difference in output characteristics of the gas concentration sensor between when the gas mixture is in the rich state and when it is in the lean state.

In the preferred mode of the invention, the gas concentration measuring apparatus may further include an identification signal generator working to generate an identification signal identifying an error inherent in the sensor output of the gas concentration sensor. The correcting circuit works to analyze the identification signal and determine one of the rich and lean correction factors which compensates for the error of the sensor output.

The correcting circuit may store therein data on a relation between a value of the identification signal and a combination of the rich and lean side correction factors. The correction circuit looks up the data to search one of the rich and lean side correction factor matching a value of the identification signal, as generated by the identification signal generator.

The correcting circuit may work to sample a value of the sensor output when the gas mixture is placed in a given atmosphere whose concentration is known. The correcting circuit determines the one of the rich and lean side correction factors based on a comparison between the sampled value of the sensor output and a corresponding reference sensor output that is expected to be a correct value attained when the gas mixture is placed in the given atmosphere.

The gas concentration sensor may be designed to produce the sensor output as a function of a concentration of an exhaust gas of a combustion engine introduced into the gas concentration sensor through the diffusion resistance layer. The correcting circuit stores therein a predefined relation between a value of the sensor output when the exhaust gas is in a given reference atmosphere wherein an air-fuel ratio of a mixture supplied to the engine is in a lean region and a value of the sensor output when the exhaust gas is in a given rich state. The correcting circuit samples an actual value of the sensor output when the exhaust gas reaches the given reference atmosphere, estimates an actual value of the sensor output when the exhaust gas is in the rich state by looking up the predefined relation, and determines the rich and lean side correction factors based on comparison between the sampled actual value and a corresponding reference output of the gas concentration sensor and between the estimated actual value and a corresponding output of the gas concentration sensor.

The given reference atmosphere may be a surrounding air atmosphere.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 21 is a map table which lists combinations of lean and rich side correction factors to be selected by an identification voltage for use in correcting an output of a sensor control circuit of the fourth embodiment;

DESCRIPTION OF THE PREFERRED EMBODIMENTS

Figure 1:
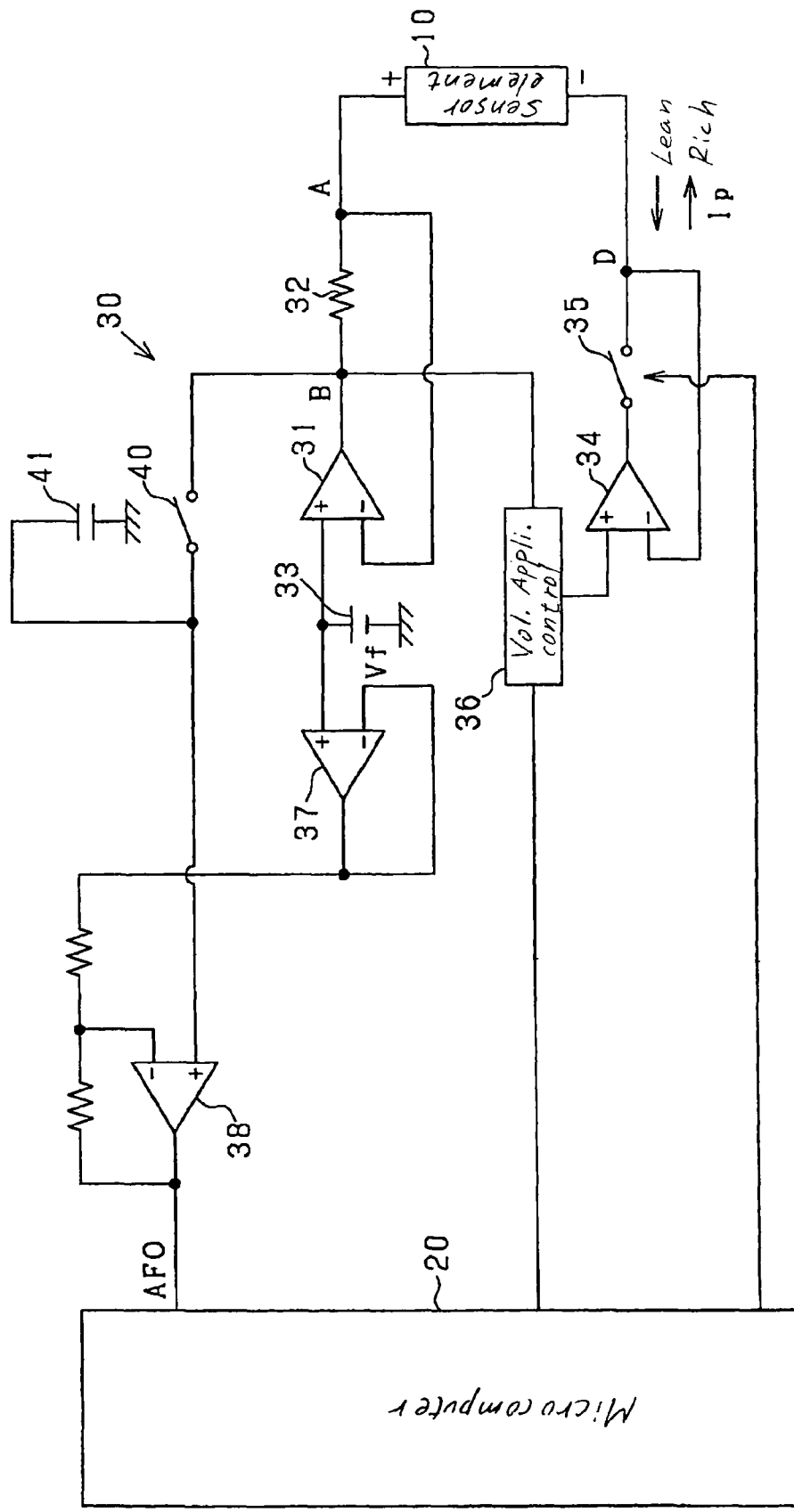
FIG. 1 is a circuit diagram which shows an electric structure of a gas concentration measuring apparatus according to the first embodiment of the invention.

Referring to the drawings, wherein like reference numbers refer to like parts in several views, particularly to FIG. 1, there is shown a gas concentration measuring apparatus designed to measure the concentration of oxygen ($O_2$) contained in exhaust emissions of an automotive engine which corresponds to an air-fuel ratio of a mixture supplied to the engine. The measured concentration is used in an air-fuel ratio control system implemented by an engine electronic control unit (ECU). The air-fuel ratio control system works to perform a stoichiometric burning control to regulate the air-fuel ratio of the mixture around the stoichiometric air-fuel ratio under feedback control and a lean-burn control to bring the air-fuel ratio to within a given lean range under feedback control.

The gas concentration measuring apparatus includes a microcomputer 20, a sensor control circuit 30, and an oxygen sensor (will be referred to as an air-fuel (A/F) sensor below) which works to produce a current signal as a function of concentration of oxygen contained in exhaust emissions introduced into a gas chamber formed in the A/F sensor.

Figures 2A, 2B:
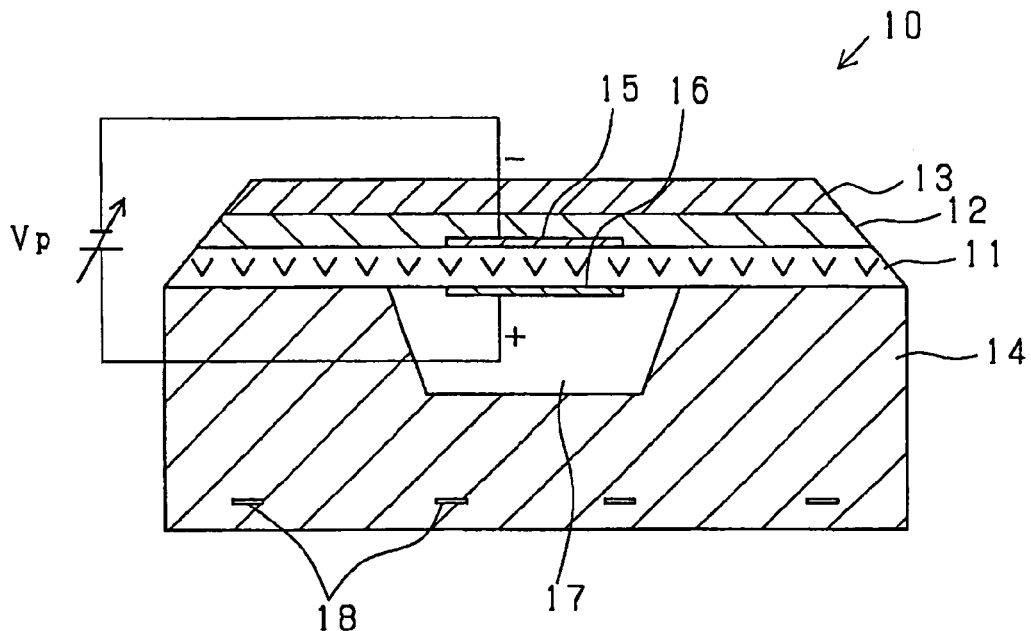
FIG. 2(a) is a transverse sectional view which shows a sensor element used in the gas concentration measuring apparatus as illustrated in FIG. 1.
FIG. 2(b) is a partially vertical sectional view of FIG. 2(a) which shows an operation of the sensor element.

The A/F sensor includes a laminated sensor element 10 which has a sectional structure, as illustrated in FIG. 2(a). The sensor element 10 has a length extending perpendicular to the drawing surface of FIG. 2(a) and is, in practice, disposed within a sensor housing and a protective cover. The A/F sensor is installed in an exhaust pipe of the engine. For instance, EPO 987 546 A2, assigned to the same assignee as that of this application teaches a structure and control of an operation of this type of gas sensor in detail, disclosure of which is incorporated herein by reference.

The sensor element 10 is made up of a solid electrolyte layer 11, a diffusion resistance layer 12, a shielding layer 13, and an insulating layer 14 which are laminated vertically as viewed in the drawing. The sensor element 10 is surrounded by a protective layer (not shown). The solid electrolyte layer 11 is made of a rectangular partially-stabilized zirconia sheet and has upper and lower electrodes 15 and 16 affixed to opposed surfaces thereof. The electrodes 15 and 16 are made of platinum (Pt), for example. The diffusion resistance layer 12 is made of a porous sheet which permits exhaust gasses to flow to the electrode 15. The shielding layer 13 is made of a dense sheet which inhibits the exhaust gasses from passing therethrough. The layers 12 and 13 are each formed using a sheet made of ceramic such as alumina or zirconia and have average porosities, or gas permeability different from each other.

The insulating layer 14 is made of ceramic such as alumina or zirconia and has formed therein an air duct 17 to which the electrode 16 is exposed. The insulating layer 14 has a heater 18 embedded therein. The heater 18 is made of heating wire which is supplied with power from a storage battery installed in the vehicle to produce heat the whole of the sensor element up to a desired activation temperature. In the following discussion, the electrode 15 will also be referred to as a diffusion resistance layer side electrode, and the electrode 16 will also be referred to as an atmosphere side electrode. The atmosphere side electrode 16 is connected to a positive (+) terminal of a power source, while the diffusion resistance layer side electrode 15 is connected to a negative (−) terminal of the power source.

The exhaust gasses flowing within an exhaust pipe of the engine to which the sensor element 10 is exposed enter and pass through the side of the diffusion resistance layer 12 and reach the electrode 15, as schematically shown in FIG. 2(b). When the exhaust gasses are in a fuel lean state (more oxygen), oxygen molecules contained in the exhaust gasses are decomposed or ionized by application of voltage between the electrodes 15 and 16, so that they are discharged to the air duct 17 through the solid electrolyte layer 11 and the electrode 16. This will cause a positive current to flow from the atmosphere side electrode 16 to the diffusion resistance layer side electrode 15. Alternatively, when the exhaust gasses are in a fuel rich state (less oxygen), oxygen molecules contained in air within the air duct 17 are ionized by the electrode 16 so that they are discharged into the exhaust pipe through the solid electrolyte layer 11 and the electrode 15 and undergo catalytic reaction with unburned components such as HC, CO, or $H_2$ in the exhaust gasses. This will cause a negative current to flow from the diffusion resistance layer side electrode 15 to the atmosphere side electrode 16. The A/F sensor is also called a lambda sensor whose operation is well known in the art, and explanation thereof in detail will be omitted here.

Figure 3:
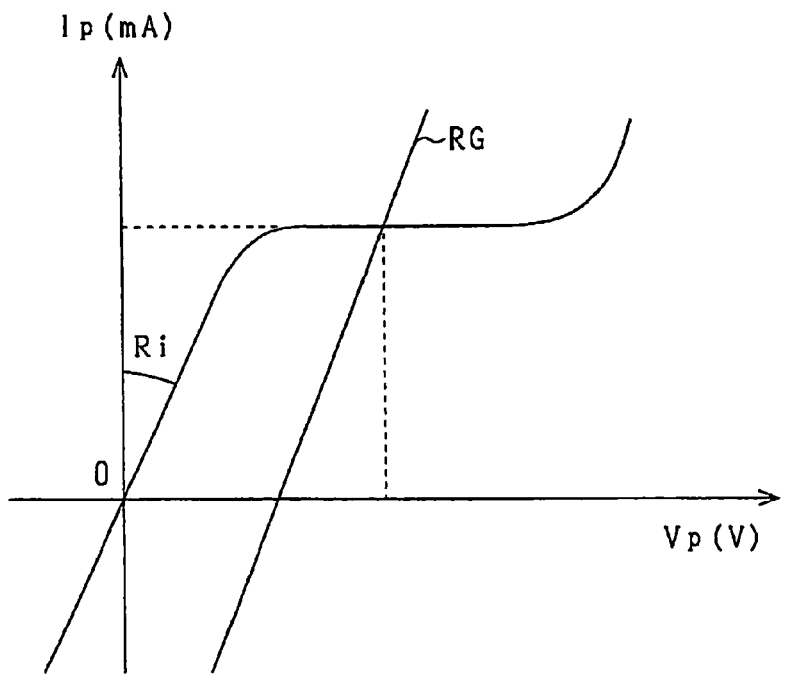
FIG. 3 shows an example of an applied voltage-to-output current map for use in determining a target voltage to be applied to the sensor element as illustrated in FIG. 2.

FIG. 3 shows a voltage-to-current relation (i.e., V-I characteristic) of the A/F sensor. A straight segment of a V-I curve extending parallel to the abscissa axis (i.e., V-axis) indicate a limiting current range within which the sensor element 10 produces an electric current Ip (i.e., a limiting current) as a function of an air-fuel ratio (i.e., richness or leanness). Specifically, as the air-fuel ratio changes to the lean side, the current Ip produced by the sensor element 10 increases, while as the air-fuel ratio changes to the rich side, the current Ip decreases. The current Ip will also be referred to as a sensor element current below.

A portion of the V-I curve lower in voltage than the limiting current range is a resistance-dependent range. An inclination of a first-order segment of the V-I curve depends upon dc internal resistance Ri of the sensor element 10. The dc internal resistance Ri changes with a change in temperature of the sensor element 10. Specifically, it increases with a decrease in temperature of the sensor element 10, so that the inclination of the first-order segment of the V-I curve in the resistance-dependent range is decreased. Alternatively, when the temperature of the sensor element 10 rises, it results in a decrease in the dc internal resistance Ri, so that the inclination of the first-order segment of V-I curve is increased. A line RG indicates a target voltage Vp to be applied to the sensor element 10 (i.e., the electrodes 15 and 16).

Referring back to FIG. 1, the gas concentration measuring apparatus, as described above, includes the sensor control circuit 30 and the microcomputer 20 and works to control an operation of the A/F sensor to determine an air-fuel ratio of a mixture supplied to the engine and also calculate the impedance Zac of the sensor element 10 (which will also be referred to as a sensor element impedance below).

The microcomputer 20 is made of a known arithmetic logic unit consisting of a CPU, memories, A/D converters, and I/O ports and works to sample an analog sensor signal, as produced by the sensor control circuit 30, through the A/D converter to determine the A/F ratio and the sensor element impedance Zac. The A/F ratio, as determined by the microcomputer 20, is outputted to the engine ECU (not shown) for use in the air-fuel ratio feedback control.

The sensor control circuit 30 connects with the sensor element 10 through a positive (+) terminal and a negative (−) terminal. The positive terminal leads to the atmosphere side electrode 16 of the sensor element 10, while the negative terminal leads to the diffusion resistance layer side electrode 15. The sensor control circuit 30 also includes operational amplifiers 31 and 34, a current-measuring resistor 32, a reference voltage source 33, a switch 35, and a voltage application control circuit 36. The positive terminal of the sensor element 10 also connects with the reference voltage circuit 33 through the current-measuring resistor 32 and the operational amplifier 31. The negative terminal also connects with the voltage application control circuit 36 through the operational amplifier 34 and the switch 35. The voltage appearing at a junction A of an end of the current-measuring resistor 32 and the positive terminal of the sensor element 10 is kept at the same level as that of the reference voltage source 33 (i.e., a reference voltage Vf of 2.2 V, for example). The sensor element current Ip flows through the current-measuring resistor 32. The voltage appearing at a junction B changes with a change in the sensor element current Ip. When the exhaust gas of the engine is in a fuel lean state, that is, the exhaust gas results from burning of a lean mixture, and the switch 35 is in an on-state or closed, the sensor element current Ip flows from the positive terminal to the negative terminal through the sensor element 10, so that the voltage at the junction B rises. Conversely, when the exhaust gas is a fuel rich state, the sensor element current Ip flows from the negative terminal to the positive terminal through the sensor element 10, so that the voltage at the junction B decreases.

The voltage application control circuit 36 works to monitor the voltage at the junction B and determine the target voltage Vp to be applied to the sensor element 10 as a function of the monitored voltage, for example, by look-up using the target applying voltage line RG, as illustrated in FIG. 3. The voltage application control circuit 36 then controls the operational amplifier 34 and the switch 35 to bring the voltage at the junction D into agreement with the target voltage Vp. If it is required only to measure the A/F ratio (i.e., the sensor element current Ip) near the stoichiometric one, the voltage application control circuit 36 may keep the voltage to be applied to the sensor element 10 at a constant level.

The sensor control circuit 30 also includes operational amplifiers 37 and 38. The reference voltage source 33 connects with the operational amplifier 37. The operational amplifier 38 works as a differential amplifier having a given amplification factor to which an output of the operational amplifier 37 and the voltage at the junction B are inputted. Specifically, the operational amplifier 38 amplifies a difference between the reference voltage Vf and the voltage at the junction B and outputs it as an A/F output voltage AFO to the microcomputer 20. The operational amplifier 38 may alternatively be designed to receive the voltages developed at the junctions A and B in order to amplify the difference between the reference voltage Vf and the voltage at the junction B. This arrangement, however, encounters the drawback in that the feedback current of the operational amplifier 38 flows through the current-measuring resistor 32, which may lead to an error in determining the A/F ratio. In order to avoid this, the operational amplifier 38 is designed to receive the output of the operational amplifier 37 and the voltage at the junction B to have the operational amplifier 37 function as a feedback current absorber in order to maintain the reliability in determining the A/F ratio.

The sensor control circuit 30 also includes a switch 40 and a capacitor 41 which are disposed between the junction B and the operational amplifier 38. When an impedance measuring mode, as will be discussed later in detail, is entered, the switch 40 is turned off or opened to retain the voltage at the junction B in the capacitor 41. This eliminates an undesirable change in output of the operational amplifier 38 which arises from sweeping of voltage applied to the sensor element 10 to measure the impedance of the sensor element 10 and results in an error in determining the A/F ratio and also ensures a correct A/F output (i.e., a current signal immediately before the switch 40 is turned off.

The microcomputer 20 works to sample the A/F output voltage AFO through the A/D port and determine an instantaneous value of the A/F ratio of a mixture supplied to the engine for use in the air-fuel ratio feedback control.

The microcomputer 20 also works to sweep the voltage applied to the sensor element 10 instantaneously in an ac form to determine the sensor element impedance Zac (i.e., an internal resistance of the sensor element 10) using a resulting change in the current Ip flowing through the sensor element 10. Specifically, when an impedance measuring mode, as will be described later, is entered, the microcomputer 20 outputs an impedance measuring command signal to the voltage application control circuit 360. The voltage application control circuit 36 then applies the voltage to the sensor element 10 and change it (i.e., the voltage at the junction D) in sequence by a given level (e.g., 0.2V) to the positive and negative sides. This causes the sensor element current Ip flowing through the sensor element 10 to change, thus resulting in a change in voltage developed at the junction B. The microcomputer 20 monitors the change in voltage at the junction B, calculates a current change $\Delta I$ by dividing the monitored change by a resistance value of the current-measuring resistor 32, and divides a change in voltage $\Delta V$ applied to the sensor element 10 by the current change $\Delta I$ to determine the sensor element impedance Zac ($=\Delta V/\Delta I$). The determination of the sensor element impedance Zac may alternatively be made by supplying the current to the sensor element 10, sweeping it in an ac form, and monitoring a resultant change in current or voltage provided by the sensor element 10. U.S. Pat. No. 6,578,563 B2, issued Jun. 17, 2003, assigned to the same assignee as that of this application teaches how to determine the sensor element impedance Zac, disclosure of which is incorporated herein by reference.

The determination of the sensor element impedance Zac is performed at a preselected regular time interval. Specifically, the microcomputer 20, as described above, outputs the impedance measuring command signal to the voltage application control circuit 36 in a cycle of 128 msec, for example. The microcomputer 20 also works to control an electric power supplied to the heater 18 so as to keep the sensor element impedance Zac at a given target value so that the sensor element 10 is held at a selected temperature (e.g., 750° C.) to maintain a desired activation status where the sensor element 10 produces an output as a function of the A/F ratio correctly.

Figure 4:
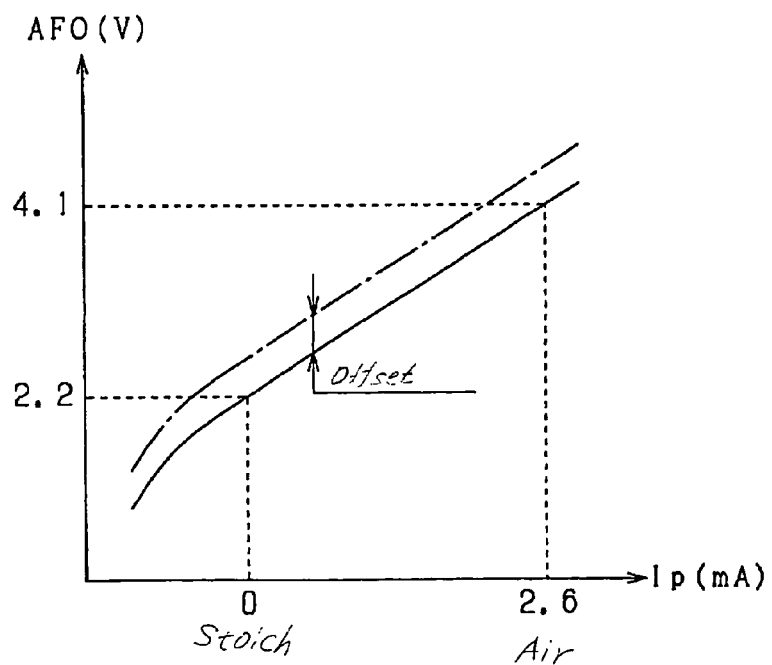
FIG. 4 is a graph which demonstrates an offset error inherent in an output of a sensor control circuit of the gas concentration measuring apparatus of FIG. 1.

Usually, the A/F sensor and the sensor control circuit 30 each have individual variability or unit-to-unit variation in characteristics thereof which may result in decreased accuracy of output of the A/F sensor. FIG. 4 demonstrates output characteristics of the A/F sensor, that is, a change in the A/F output voltage AFO in terms of a change in the sensor element current Ip. A solid line indicates reference output characteristics or desired reference value of the A/F output voltage AFO. A broken line indicates actual output characteristics or actually attained value of the A/F output voltage AFO which has a difference or offset error between itself and the reference value, as indicated by the solid line. The reference output characteristics show that when the exhaust gas of the engine is in an atmosphere where an A/F ratio of a mixture supplied to the engine is stoichiometric (i.e., Ip=0 mA), the A/F output voltage AFO is 2.2V, and when it is in an atmosphere where a mixture equivalent to surrounding air is supplied to the engine (i.e., Ip=2.6 mA), the A/F output voltage AFO is 4.1V. The actual output characteristics show that an actual value of the A/F output voltage AFO is greater than the reference value by the offset error. The microcomputer 20 is designed to correct the A/F output voltage AFO to compensate for the offset error in order to ensure the accuracy of measurement in the gas concentration measuring apparatus.

The microcomputer 20 of this embodiment is designed based on the above fact that when the exhaust gas is stoichiometric, the sensor element current Ip will be 0 mA, and the reference value of the A/F output voltage AFO is selected to 2.2V. Specifically, the microcomputer 20 is designed to bring the sensor control circuit 30 into a virtual stoichiometric AFR measuring mode, as will be described later in detail, and samples the offset error. In practice, the microcomputer 20 turns off or opens the switch 35 temporarily during running of the engine, samples an instantaneous value of the A/F output voltage AFO, and calculates an offset error using the sampled value of the A/F output voltage AFO as a sensor output correction factor for use in eliminating an error in the A/F output voltage AFO.

Figure 5:
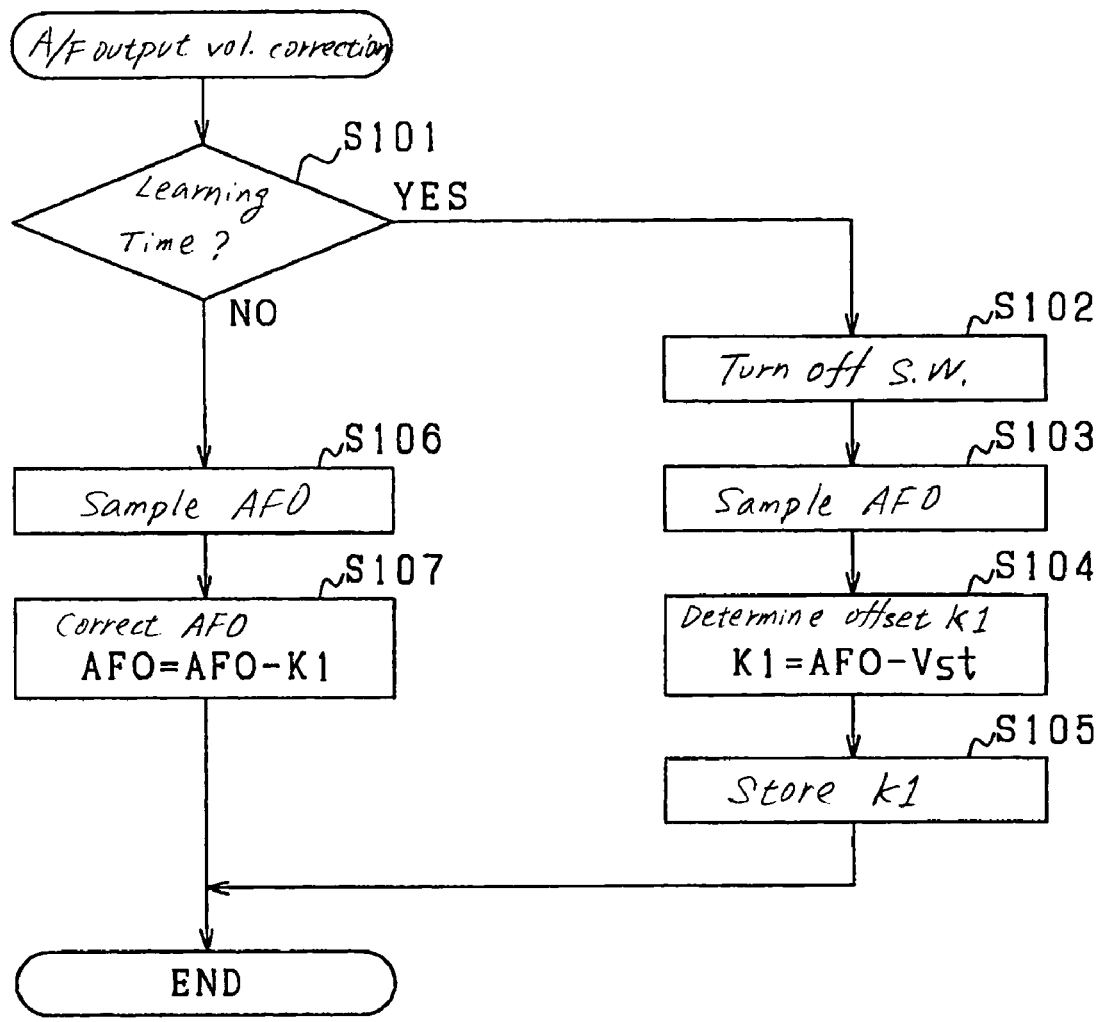
FIG. 5 is a flowchart of a program to be executed in the gas concentration measuring apparatus of FIG. 1 to compensate for the offset error, as indicated in FIG. 4.

FIG. 5 is a flowchart of a sequence of logical steps or program to be executed by the microcomputer 20 to correct the A/F output voltage AFO using the offset error. This program is performed at a preselected regular interval.

After entering the program, the routine proceeds to step 101 wherein it is determined whether a leaning time has been reached or not. The leaning time is a time when the sensor control circuit 30 should be placed in the virtual stoichiometric AFR measuring mode to lean the offset error. The leaning time is determined to have been entered every lapse of a period of time of, for example, 10 minutes, a few ten minutes, or a few hours. The learning time may alternatively be determined to have been entered when the A/F output voltage AFO is not used in the air-fuel ratio feedback control, for example, before the A/F sensor becomes activate, during a fuel cut-off mode of the engine, or when a main relay is controlled to keep the microcomputer 20 turned on for a given short period of time after an ignition switch of the vehicle is turned off.

If a YES answer is obtained in step 101, then the routine proceeds to step 102 wherein an off-switching signal is outputted to the switch 35 to open it for a preselected period of time (e.g., 5 msec.). The routine proceeds to step 103 wherein an instantaneous value of the A/F output voltage AFO is sampled. The routine proceeds to step 104 wherein an offset error K1 is determined by subtracting a stoichiometric AFR reference voltage Vst from the value of the A/F output voltage AFO, as sampled in step 103. Note that the stoichiometric AFT reference voltage Vst is a correct value of the A/F output voltage AFO which is to be attained when the exhaust gas is at the stoichiometric A/F ratio and set to 2.2V in this embodiment.

The routine proceeds to step 105 wherein the offset error K1, as calculated in step 104, is stored in a standby RAM installed in the microcomputer 20.

If a NO answer is obtained in step 101 meaning that the learning time is not yet reached, then the routine proceeds to step 106 wherein an instantaneous value of the A/F output voltage AFO is sampled. Specifically, during a time other than the learning time, the sensor control circuit 30 is placed in an AFR measuring mode in which the sensor element current Ip (i.e., the A/F output voltage AFR) is sampled to determine an instantaneous value of the A/F ratio of a mixture being supplied to the engine. The routine proceeds to step 107 wherein the value of the A/F output voltage AFO, as sampled in step 106, is corrected using the offset error K1, as stored in step 105. Specifically, the offset error K1 is subtracted from the value of the A/F output voltage AFO to produce an A/F ratio signal indicative of the air-fuel ratio of mixture supplied the engine for use in the air-fuel ratio feedback control.

Figure 16A:
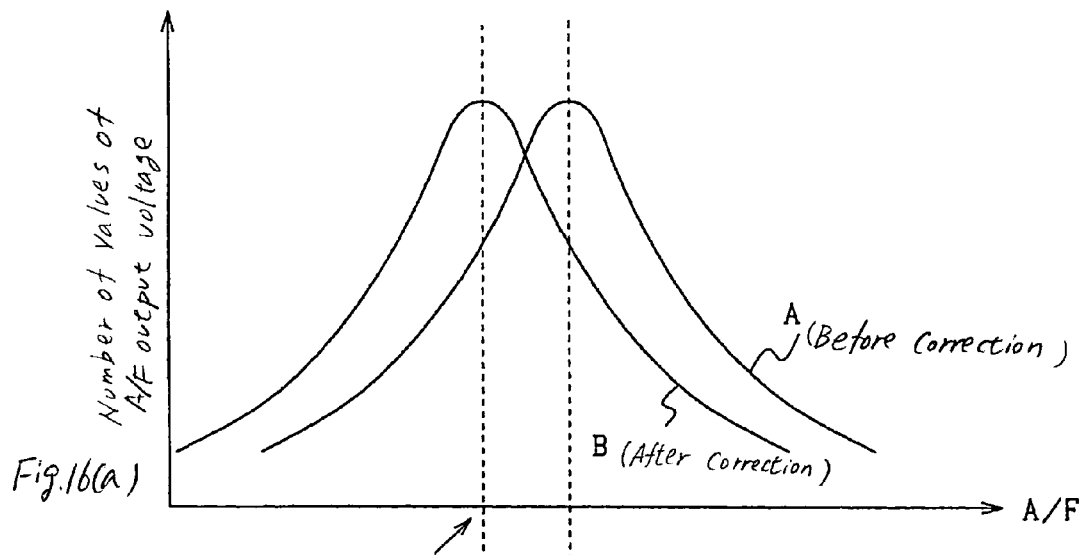
FIG. 16(a) is a graph which demonstrates distributions of values of an A/F output voltages, as produced by a sensor control circuit, before and after they are corrected.
Figure 16B:
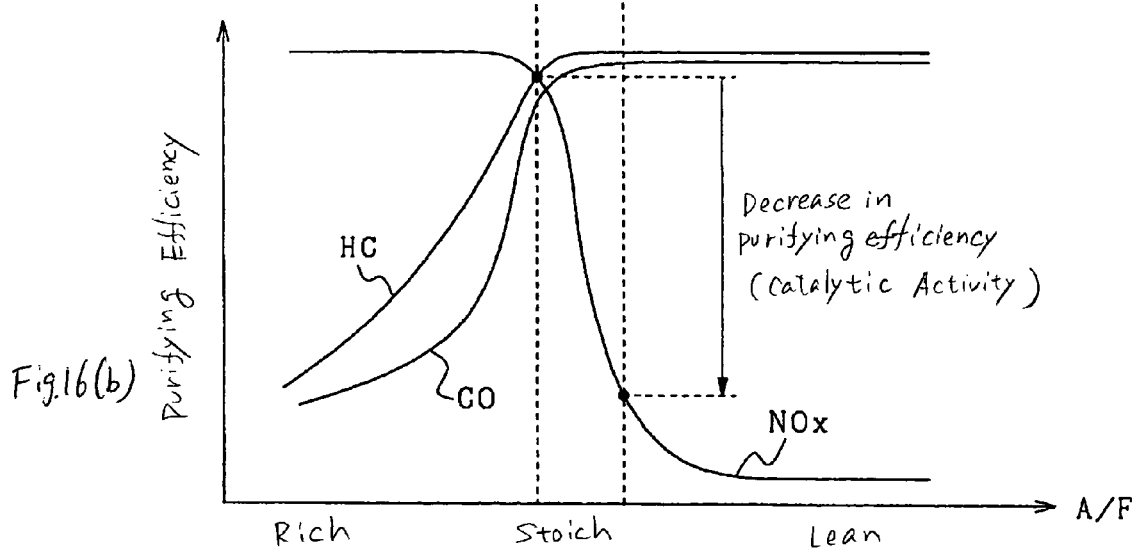
FIG. 16(b) is a graph which demonstrates distributions of catalytic activities to purify harmful emissions of an engine.

The gas concentration measuring apparatus of this embodiment is, as can be seen from the above discussion, designed to open the switch 35 to place the sensor control circuit 30 in the virtual stoichiometric AFR measuring mode that is a condition equivalent to where the sensor element 10 is exposed to the exhaust gas arising from burning of a stoichiometric mixture in the engine and sample an instantaneous value of the A/F output voltage AFO to determine or learn the offset error K1. The gas concentration measuring apparatus then corrects the value of the A/F output voltage AFO using the offset error K1 to determine an air-fuel ratio of a mixture being supplied to the engine and uses it in the air-fuel ratio feedback control. This improves the accuracy of the air-fuel ratio feedback control and the quality of exhaust emissions of the engine. Usually, when the engine is being operated at the stoichiometric A/F ratio, it results in, as shown in FIGS. 16(a) and 16(b), maximized efficiency of purifying HC, CO, and NOx contained in the exhaust gas. However, when the gas concentration measuring apparatus has the output characteristics, as indicated by the broken line in FIG. 4, that is, when the A/F output voltage AFO is not corrected, as denoted by a line A in FIG. 16(a), it will result in a reduction in efficiency of purifying HC, CO, and HOx (i.e., the catalytic activity of the catalytic converter installed in the exhaust system of the engine). The gas concentration measuring apparatus of this embodiment, thus, serves to keep the activity of the catalytic converter maximized.

The gas concentration measuring apparatus works to update the offset error K1 cyclically, thereby permitting the A/F output voltage AFO to be corrected correctly immediately even after start-up of the engine.

Figure 6:
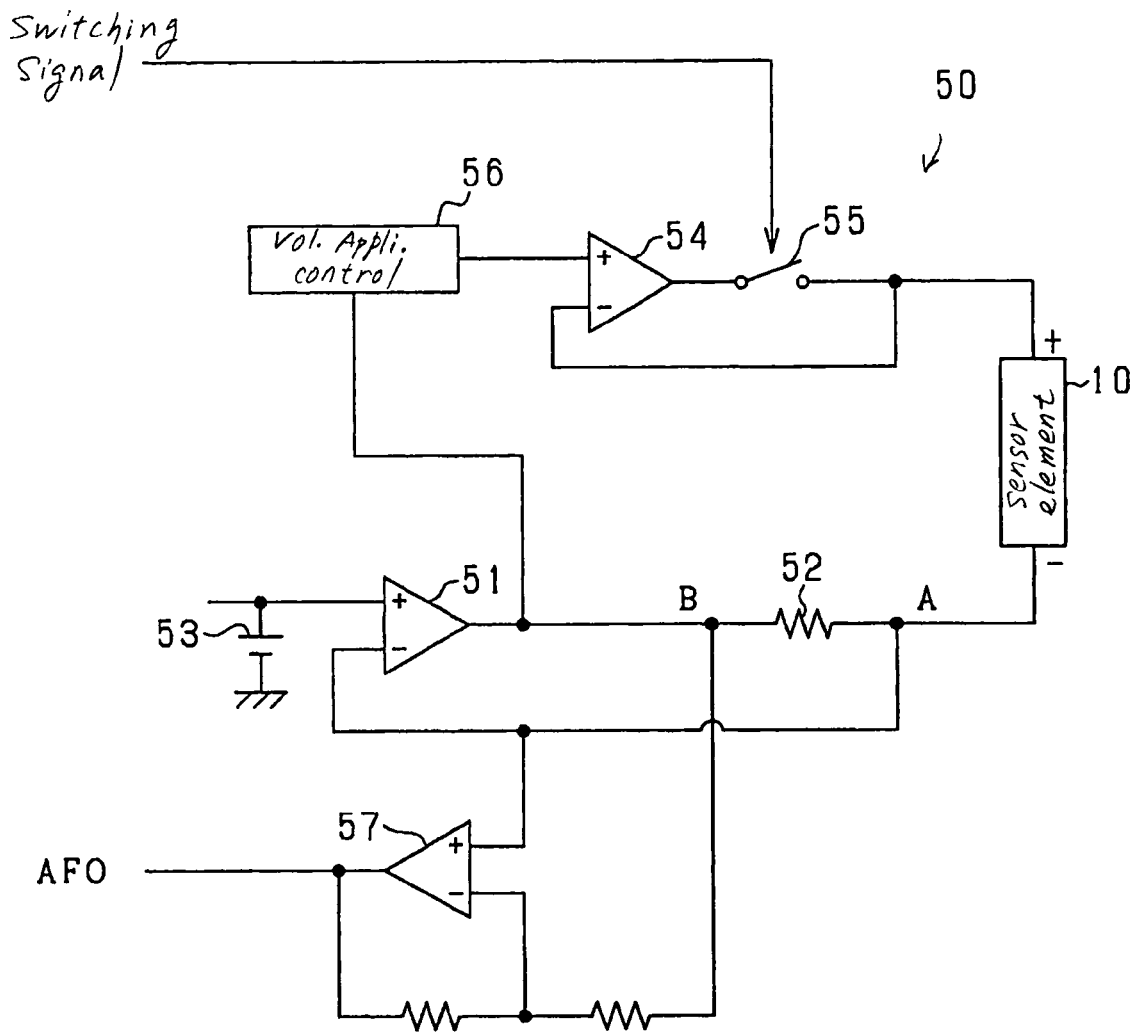
FIG. 6 is a circuit diagram which shows a modification of the sensor control circuit of the gas concentration measuring apparatus of FIG. 1.

FIG. 6 shows a sensor control circuit 50 which has a structure in which circuit components leading to the positive and negative terminals of the sensor element 10 are reversed to those in FIG. 1.

The reference voltage source 53 is connected to the negative terminal of the sensor element 10 through the operational amplifier 51 and the current-measuring resistor 52. The voltage application control circuit 56 is connected to the positive terminal of the sensor element 10 through the operational amplifier 54 and the switch 55. The voltage appearing at the junction A is kept at a level identical with a reference voltage (e.g., 2.2V), as produced by the reference voltage source 52. The sensor element current Ip flows through the current-measuring resistor 52 to change the voltage developed at the junction B as a function of the sensor element current Ip. When the exhaust gas is lean, the sensor element current Ip flows from the positive to negative terminal, so that the voltage at the junction B drops. Conversely, when the exhaust gas is rich, the sensor element current Ip flows from the negative to positive terminal, so that the voltage at the junction B rises.

The voltage application control circuit 56 works to monitor the voltage developed at the junction B and determines a target level of voltage to be applied to the sensor element 10 as a function of the monitored voltage. The operational amplifier 57 connects with the junctions A and B and works to output the A/F output voltage AFO to the microcomputer 20, as illustrated in FIG. 1.

The microcomputer 20 works to execute the program of FIG. 5 to learn the offset error K1 for correcting the A/F output voltage AFO in the same manner as described above. Specifically, the microcomputer 20 opens the switch 55 to bring the sensor control circuit 50 into the virtual stoichiometric AFR measuring mode, samples an instantaneous value of the A/F output voltage AFO to determine the offset error K1, and correct the value of the A/F output voltage AFO, as sampled in the AFR measuring mode, using the offset error K1.

The gas concentration measuring apparatus of the second embodiment will be described below.

Figure 7:
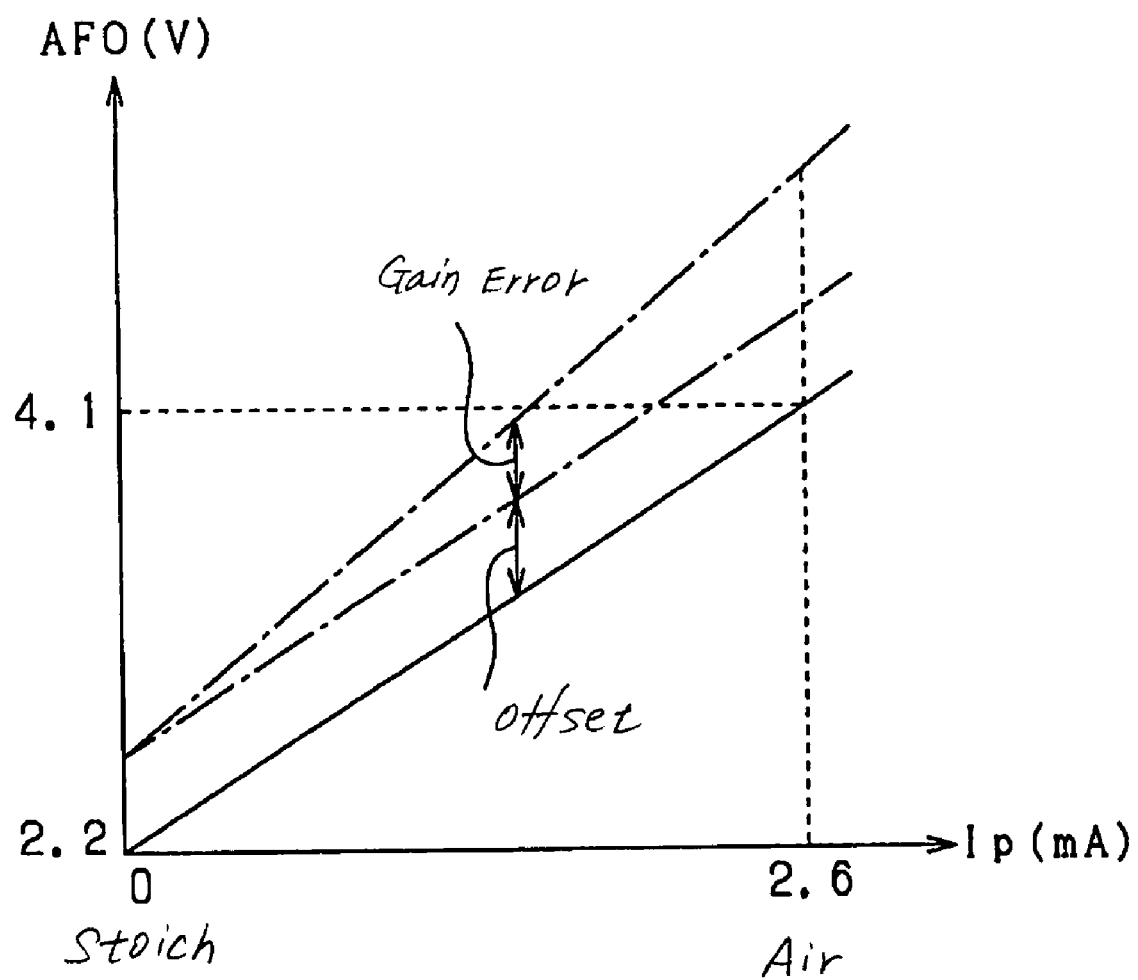
FIG. 7 is a graph which shows an offset error and a gain error which are inherent in a sensor control circuit of a gas concentration measuring apparatus according to the second embodiment of the invention.

A gain error may also arise from an error in adjustment of a gain of each of the operational amplifiers 31, 34, 37, and 38 in the structure of FIG. 1, for example. FIG. 7 demonstrates a change in gain error with a change in the sensor element current Ip. The graph shows that the gain error is zero (0) when the exhaust gas is at the stoichiometric A/F ratio and increases substantially proportional to an increase in the A/F output voltage AFO, in other words, that when the exhaust gas is in the stoichiometric state, only the offset error K1, as described above, arises, but when it is extremely lean or in an atmospheric state, both the offset error K1 and the gain error arise. The gas concentration measuring apparatus of this embodiment is, therefore, designed to sample two errors of the A/F output voltage AFO when the exhaust gas is in the stoichiometric state and in the atmospheric state and calculate a difference therebetween to determine the gain error as a correction factor used in correcting the A/F output voltage AFO.

Figure 8:
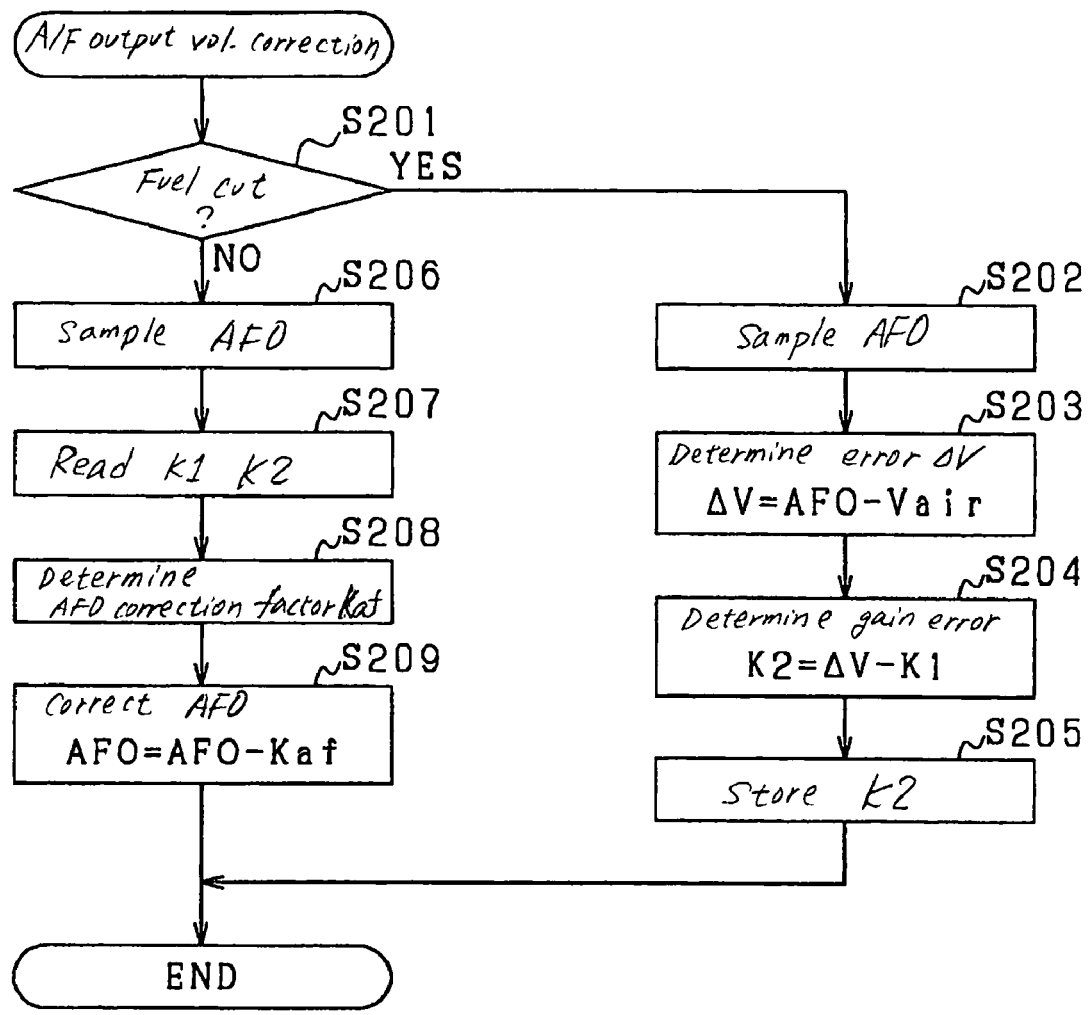
FIG. 8 is a flowchart of a program to be executed in a gas concentration measuring of the second embodiment of the invention to compensate for the offset error and gain error, as demonstrated in FIG. 7.

FIG. 8 is a flowchart of a program to be executed by the microcomputer 20 cyclically at a stated time interval to compensate for the gain error, as described above. This program is initiated after the offset error K1 is found in a manner such as described in FIG. 5 and retained in the standby RAM of the microcomputer 20.

After entering the program, the routine proceeds to step 201 wherein it is determined whether the engine is now undergoing a fuel cut or not. This determination is made to determine whether a condition which permits a gain error K2, as produced when the exhaust gas is in the atmospheric state, to be sampled is met or not. If a YES answer is obtained meaning that the gain error K2 sampling permissible condition is met, then the routine proceeds to step 202 wherein an instantaneous value of the A/F output voltage AFO is sampled. The routine proceeds to step 203 wherein an atmospheric state error $\Delta V$ is calculated by subtracting a reference voltage Vair from the value of the A/F output voltage AFO, as sampled in step 202. Note that the reference voltage Vair is a correct level of the A/F output voltage AFO which is to be attained when the exhaust gas is in the atmospheric state and set to 4.1V in this embodiment.

The routine proceeds to step 204 wherein the atmospheric state gain error K2 is calculated by subtracting the offset error K1 from the atmospheric state error $\Delta V$ (i.e., $K2=\Delta V-K1$). The routine proceeds to step 205 wherein the atmospheric state gain error K2, as derived in step 204, is stored in the standby RAM of the microcomputer 20.

If a NO answer is obtained in step 201 meaning that the engine is not undergoing the fuel cut, that is, the microcomputer 20 is in the AFR measuring mode, then the routine proceeds to step 206 wherein an instantaneous value of the A/F output voltage AFO is sampled. The routine proceeds to step 207 wherein the offset error K1 and the atmospheric state gain error K2 are read out of the standby RAM. The routine proceeds to step 208 wherein an AFO correction factor Kaf is calculated. Specifically, the gain error has zero (0) and K2 when the exhaust gas in the stoichiometric state and in the atmospheric state, respectively. A gain error K2a of the value of the A/F output voltage AFO, as sampled in step 206, is calculated by interpolating the values of the gain error when the exhaust gas in the stoichiometric state and the atmospheric state. The gain error K2a is added to the offset error K1 to derive the AFO correction factor Kaf.

The routine proceeds to step 209 wherein the value of the A/F output voltage AFO, as sampled in step 206, is corrected using the AFO correction factor Kaf, as derived in step 208. Specifically, the AFO correction factor Kaf is subtracted from the value of the A/F output voltage AFO to produce an A/F ratio signal indicative of the air-fuel ratio of a mixture being supplied the engine for use in the air-fuel ratio feedback control.

The gas concentration measuring apparatus of this embodiment is, as apparent from the above discussion, designed to sample and correct the value of the A/F output voltage AFO cyclically so as to compensate for two errors which inevitably arise in the circuit of the type as illustrated in FIG. 1 or 6, thus improving the accuracy of output of the gas concentration measuring apparatus further.

The gas concentration measuring apparatus works to update the offset error K1 and the atmospheric state gain error K2 cyclically, thus permitting the A/F output voltage AFO to be corrected correctly immediately even after start-up of the engine.

Figure 9:
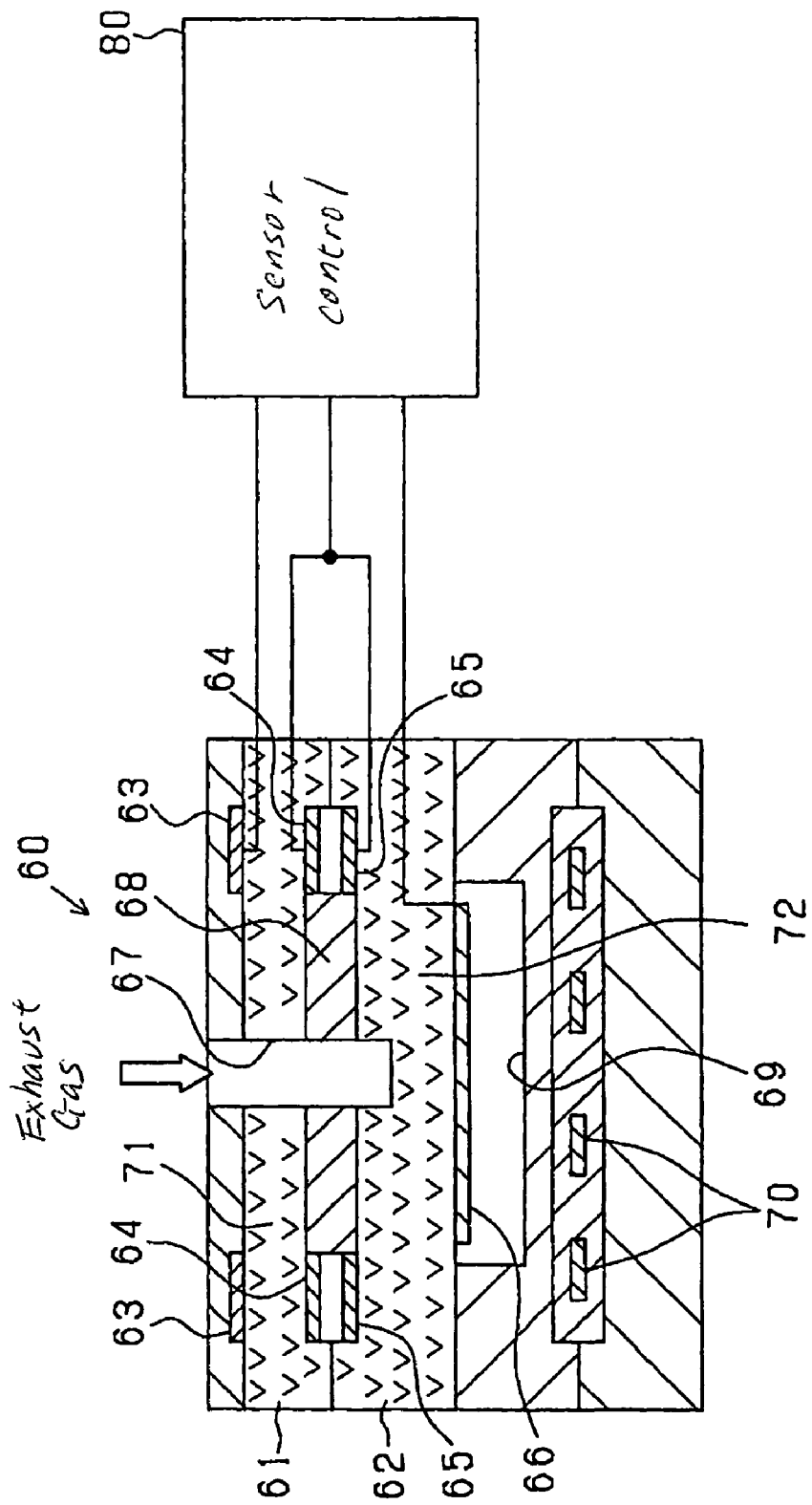
FIG. 9 is a transverse sectional view which shows a sensor element of a gas concentration measuring apparatus according to the third embodiment of the invention.

FIG. 9 shows a sensor element 60 according to the third embodiment of the invention which is different in structure from the one illustrated in FIG. 2(a) and may be fabricated in the A/F sensor as used in each of the above embodiments instead of the sensor element 10.

The sensor element 60 includes a laminate of two solid electrolyte layers 61 and 62. The solid electrolyte layer 61 has electrodes 63 and 64 affixed to opposed surfaces thereof. Similarly, the solid electrolyte layer 62 has electrodes 65 and 66 affixed to opposed surfaces thereof. Each of the electrodes 63, 64, and 65 is viewed in the drawing as being made up of right and left separate parts, but, it is, in practice, formed by a single plate having a connecting portion (not shown) extending in a transverse direction in the drawing.

The solid electrolyte layer 61 and the electrodes 63 and 64 constitute a pump cell 71. The solid electrolyte layer 62 and the electrodes 65 and 66 constitute a monitor cell 72. The electrodes 63 to 66 are joined to a sensor control circuit 80 which leads to the microcomputer 20, as illustrated in FIG. 1.

The sensor element 60 also includes a gas inlet 67 through which exhaust gasses of the automotive engine enter and a porous diffusion layer 68, an air duct 69, and a heater 70. The structure and operation of this type of sensor element are disclosed in, for example, U.S. Pat. No. 6,295,862 B1, assigned to the same assignee as that of this application, disclosure of which is incorporated herein by reference. The monitor cell 72 is generally also called an electromotive force cell or an oxygen concentration sensor cell.

The monitor cell 72 works to produce an electromotive force which has one of two discrete values (e.g., 0V and 0.9V) selectively as a function of whether the exhaust gasses are on the rich side or the lean side of a stoichiometric point corresponding to a stoichiometric air-fuel ratio of mixture supplied to the engine. When the exhaust gasses are on the lean side, the monitor cell 72 produces a lower electromotive force. Conversely, when the exhaust gasses are on the rich side, the monitor cell 72 produces a higher electromotive force. The sensor control circuit 80 works to control the voltage applied to the pump cell 71 so that an electromotive force produced by the monitor cell 72 is kept at 0.45V which corresponds to the stoichiometric point.

Figure 10:
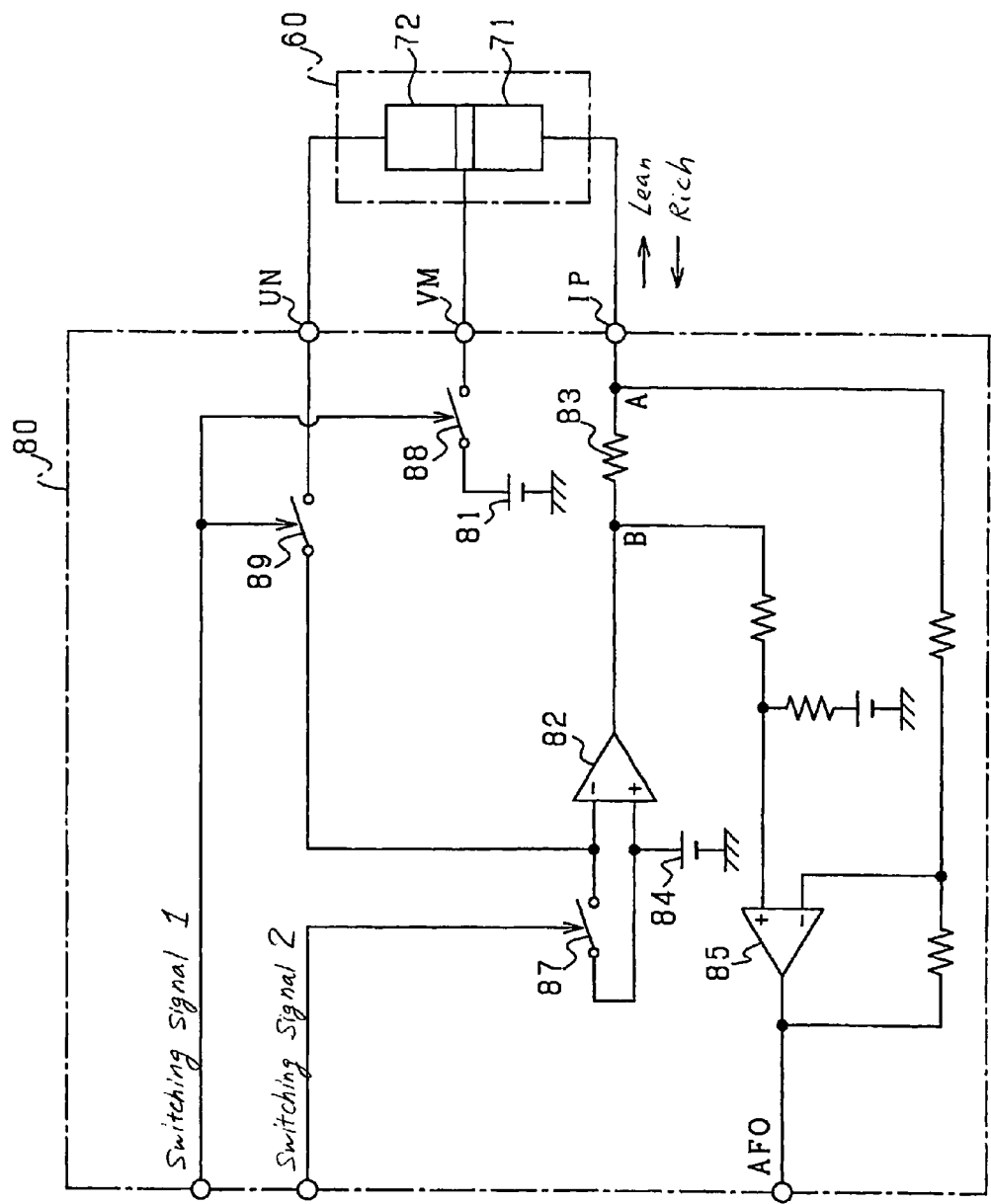
FIG. 10 is a circuit diagram which shows a sensor control circuit connected to the sensor element of FIG. 9.

FIG. 10 shows an internal structure of the sensor control circuit 80.

A terminal VM is a common terminal shared between the pump cell 71 and the monitor cell 72. The common terminal VM is connected to a reference voltage source 81 which produces a reference voltage of, for example, 2.5V. The pump cell 71 is also connected at the electrode 63 to the terminal IP. The monitor cell 72 is also connected at the electrode 66 to the terminal UN. The terminals IP and UN form a closed circuit together with the cells 71 and 72, an operational amplifier 82, and a current-measuring resistor 83. The operational amplifier 82 is connected at a noninverting input (i.e., +terminal) thereof to a reference voltage source 84 which produces a reference voltage of 3.0V.

When the exhaust gas is lean, the current Ip flows through the current-measuring resistor 83 in the direction from the junction B to the junction A. Conversely, when the exhaust gas is rich, the current Ip flows through the current-measuring resistor 83 in the direction from the junction A to the junction B. The sensor control circuit 80 also includes a feedback circuit (not shown) which works to control the voltage applied to the pump cell 71 to bring an output voltage of the monitor cell 72 into agreement with a target one. This feedback control can be of any type known in the art, and explanation thereof in detail will be omitted here.

The sensor control circuit 80 also includes an operational amplifier 85 and switches 87, 88, and 89. The operational amplifier 85 is connected to the junctions A and B across the current-measuring resistor 83 and works to output the A/F output voltage AFO to the microcomputer 20, as illustrated in FIG. 1.

The switch 87 is connected to plus and minus inputs of the operational amplifier 82. The switch 88 is connected to the common terminal VM. The switch 89 is connected to the monitor cell terminal UN. The switch 87 is of a normally open type and controlled in operation by a switching signal 1. Each of the switches 88 and 89 is of a normally closed type and controlled in operation by a switching signal 2.

In the AFR measuring mode, the sensor control circuit 80 works to open the switch 87, while closing the switches 88 and 89 to produce the A/F output voltage AFO as a function of an instantaneous air-fuel ratio of a mixture supplied to the engine. In the virtual stoichiometric AFR measuring mode, the sensor control circuit 80 works to close the switch 87, while opening the switches 88 and 89 and sample an instantaneous value of the A/F output voltage AFO to determine the offset error K1. The sensor control circuit 80 may also calculate the gain error K2 in the same manner as described in the second embodiment.

Figure 11:
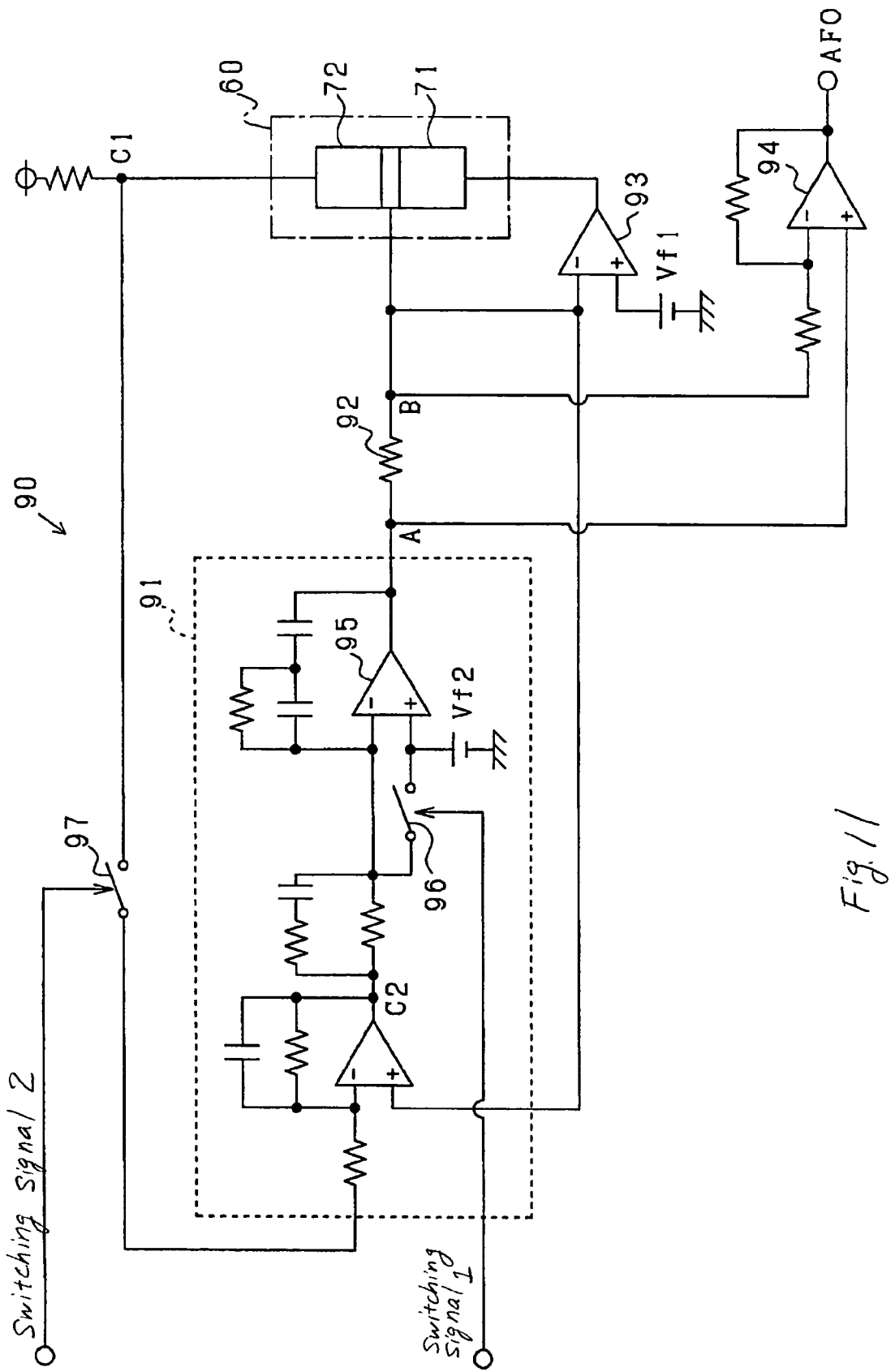
FIG. 11 is a circuit diagram which shows a modification of the sensor control circuit of FIG. 10.

In the sensor control circuit 80, the voltages developed at the junctions A and B located across the current-measuring resistor 83 both change with a change in current flowing through the current-measuring resistor 83. One of ends of the current-measuring resistor 83 may, however, be maintained constant using the structure, as illustrated in FIG. 11.

The sensor control circuit 90 includes an operational amplifier 93 through which the same voltage (e.g., 3V) as the reference voltage Vf1 is applied to a common terminal of the pump cell 71 and the monitor cell 72 of the sensor element 60. This causes the voltage appearing at the junction B to be kept at 3V, for example. The sensor control circuit 90 has a closed loop including the monitor cell 72, the feedback circuit 91, and the current-measuring resistor 92. The reference voltage Vf2 provided in the feedback circuit 91 is, for example, 2.55V.

The operation of the sensor control circuit 90 will be described taking as an example a case in which the exhaust gas of the engine is rich.

When the exhaust gas is rich, the monitor cell 72 produces an electromotive force, so that the voltage appearing at a junction C1 rises up to, for example, 3.45V, thereby causing the electric potential developed at a junction C2 in the feedback circuit 91 to drop. This causes the electric potential at the junction A to rise. Specifically, when the exhaust is rich, the sensor element current Ip flows through the current-measuring resistor 92 from the junction A to the junction B. Conversely, when the exhaust is lean, the sensor element current Ip flows through the current-measuring resistor 92 from the junction B to the junction A. The operational amplifier 94 having a stated amplification factor is connected to the junctions A and B of the current-measuring resistor 92.

The feedback circuit 91 includes the operational amplifier 95 and the switch 96. The switch 96 is connected to plus and minus inputs of the operational amplifier 95. The switch 97 is disposed between the feedback circuit 91 and the monitor cell 72. The switch 96 is of a normally open type and controlled in operation by the switching signal 1. The switch 97 is of a normally closed type and controlled in operation by the switching signal 2.

In the AFR measuring mode, the sensor control circuit 90 works to open the switch 96, while closing the switch 97 to produce the A/F output voltage AFO as a function of an instantaneous air-fuel ratio of a mixture supplied to the engine. In the virtual stoichiometric AFR measuring mode, the sensor control circuit 90 works to close the switch 96, while opening the switch 97 and sample an instantaneous value of the A/F output voltage AFO to determine the offset error K1. The sensor control circuit 90 may also calculate the gain error K2 in the same manner as described in the second embodiment.

Figure 12:
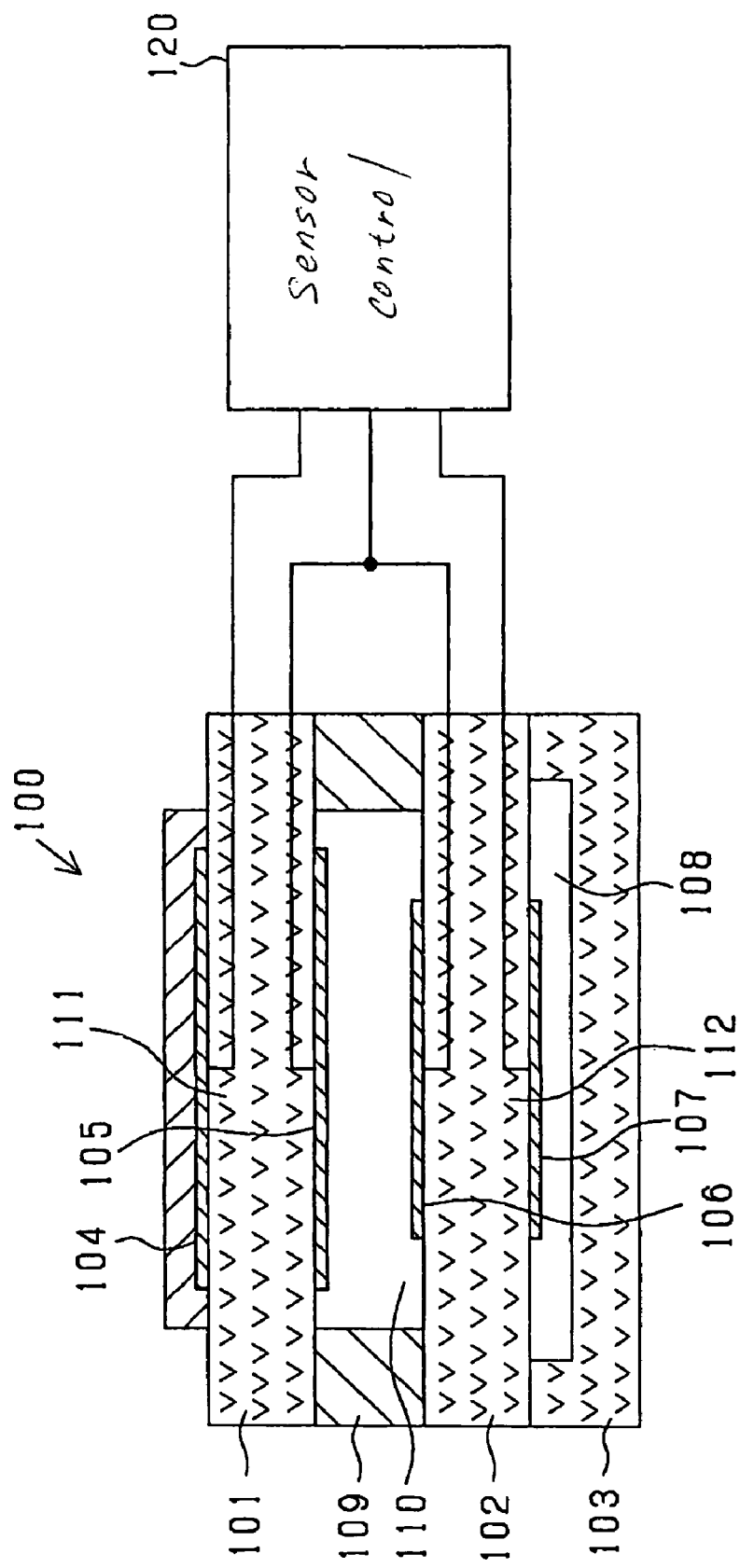
FIG. 12 is a transverse sectional view which shows a modified form of a sensor element which may be employed in a gas concentration measuring apparatus of each embodiment.

FIG. 12 shows a sensor element 100 which may be built in the A/F sensor, as employed in each of the above embodiments.

The sensor element 100 includes three solid electrolyte layers 101, 102, and 103. The solid electrolyte layer 101 has electrodes 104 and 105 affixed to opposed surfaces thereof. Similarly, the solid electrolyte layer 102 has electrodes 106 and 107 affixed to opposed surfaces thereof. The solid electrolyte layer 101 and the electrodes 104 and 105 form a pump cell 111. The solid electrolyte layer 102 and the electrodes 106 and 107 form a monitor cell 112. The solid electrolyte layer 103 forms a wall defining an oxygen reference chamber 108. The sensor element 100 is, like the sensor element 10, of a laminated structure. The sensor element 100 also includes a porous diffusion layer 109 and a gas chamber 110 into which exhaust gasses of the automotive engine enter. The monitor cell 112 operates, like the monitor cell 72 illustrated in FIG. 9, as an electromotive force cell or an oxygen concentration sensor cell.

The sensor element 10 is connected to the sensor control circuit 120. The sensor control circuit 120 may have substantially the same structure as the one illustrated in FIG. 10 or 11, and explanation thereof in detail will be omitted here.

The A/F sensor, as employed in each of the above embodiments, may also be designed to have two- or three-cell structure. The sensor element 10, 60, or 100 may be of a cup-shaped type known in the art. The A/F sensor may also be implemented by a typical $O_2$ sensor designed to produce an electromotive force between electrodes affixed to a sensor element as a function of concentration of oxygen contained in exhaust emissions of an automotive engine.

The gas concentration measuring apparatus, as described in each of the above embodiments, may be used with a composite gas concentration measuring sensor which includes first and second cells made of a solid electrolyte body. The first cell works as a pump cell to pump oxygen molecules out of or into a first gas chamber formed in a sensor body and output a signal indicative of the concentration of the pumped oxygen molecules. The second cell works as a sensor cell to produce a signal indicative of the concentration of a preselected component of gasses flowing into a second gas chamber from the first gas chamber. For example, the composite gas concentration measuring sensor may be used to measure the concentration NOx contained in exhaust gasses of the automotive engine. Further, the composite gas concentration measuring sensor may be designed to have a third cell serving as a monitor cell or a second pump cell to produce an electromotive force as a function of concentration of oxygen molecules remaining in the second gas chamber.

Figure 13:
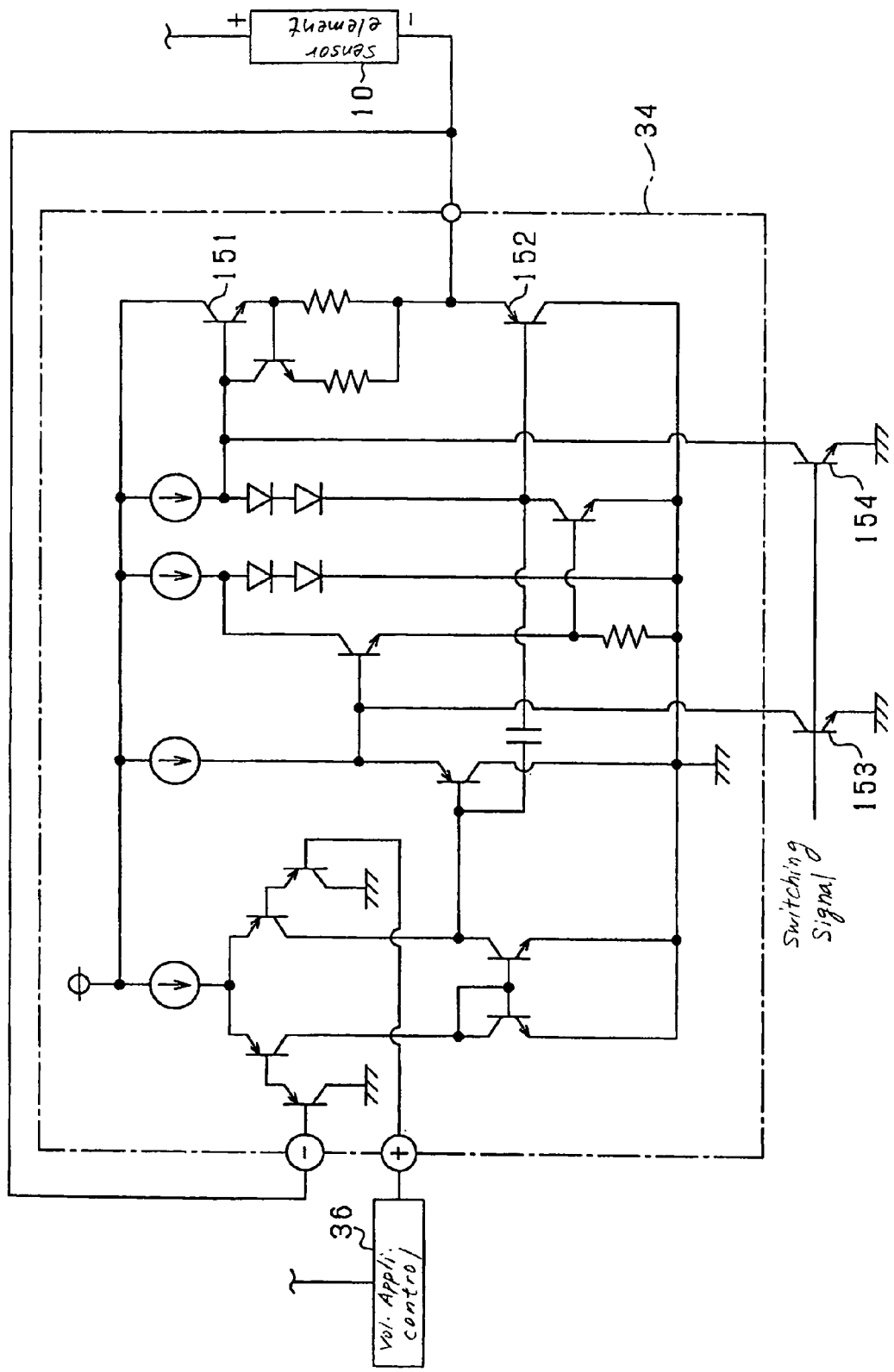
FIG. 13 is a circuit diagram which shows a second modification of a sensor control circuit.
Figure 14:
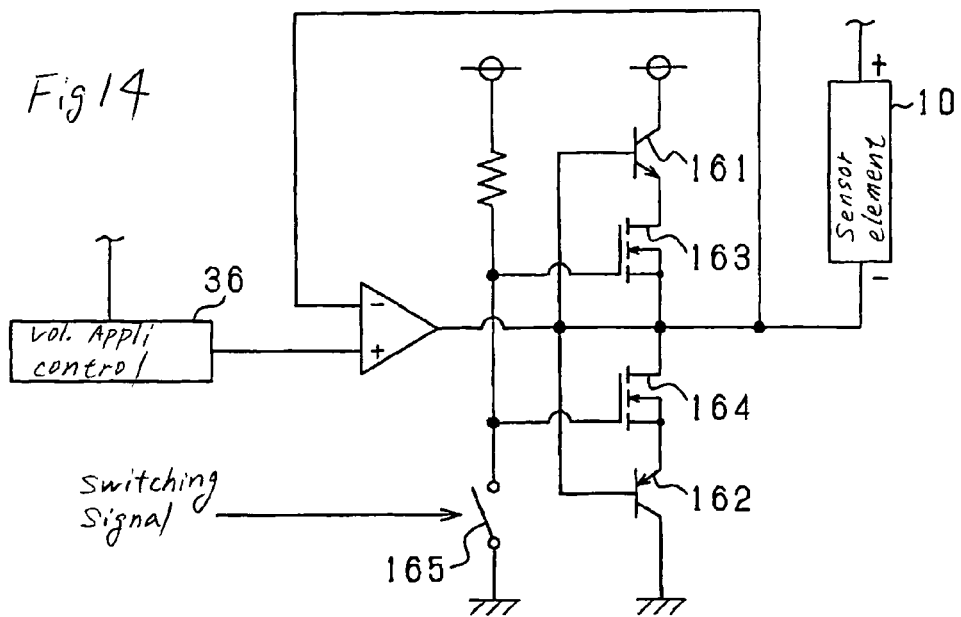
FIG. 14 is a circuit diagram which shows a third modification of a sensor control circuit.

FIGS. 13 and 14 show modifications of the sensor control circuit 30, as illustrated in FIG. 1, which work to perform the virtual stoichiometric AFR measuring mode temporarily for learning the offset error K1 and/or the gain error K2, as described above.

FIG. 13 illustrates an internal structure of the operational amplifier 34 of FIG. 1 which leads to the minus terminal of the sensor element 10. The operational amplifier 34 includes transistors 151 and 152 which are switched in operation modes by transistors 153 and 154. Specifically, the microcomputer 20 outputs switching signals in an on-state to the transistors 153 and 154 to turn off the transistors 151 and 152, thereby bringing the sensor control circuit 30 into the virtual stoichiometric AFR measuring mode temporarily.

FIG. 14 illustrates a modified form only of a portion of the sensor control circuit 30 which leads to the minus terminal of the sensor element 10. MOSFETs 163 and 164 are connected to each other across the minus terminal of the sensor element 10 between transistors 161 and 162. The microcomputer 20 outputs a switching signal to a switch 165 to control an input to gates of the MOSFETs 163 and 164. Specifically, when it is required to place the sensor control circuit 30 in the virtual stoichiometric AFR measuring mode, the microcomputer 20 outputs the switching signal in the on-state to close the switch 165 to turn off the MOSFETs 163 and 164, thereby opening a circuit loop leading to the minus terminal of the sensor element 10 to bring the sensor control circuit 30 into the virtual stoichiometric AFR measuring mode.

Figure 15:
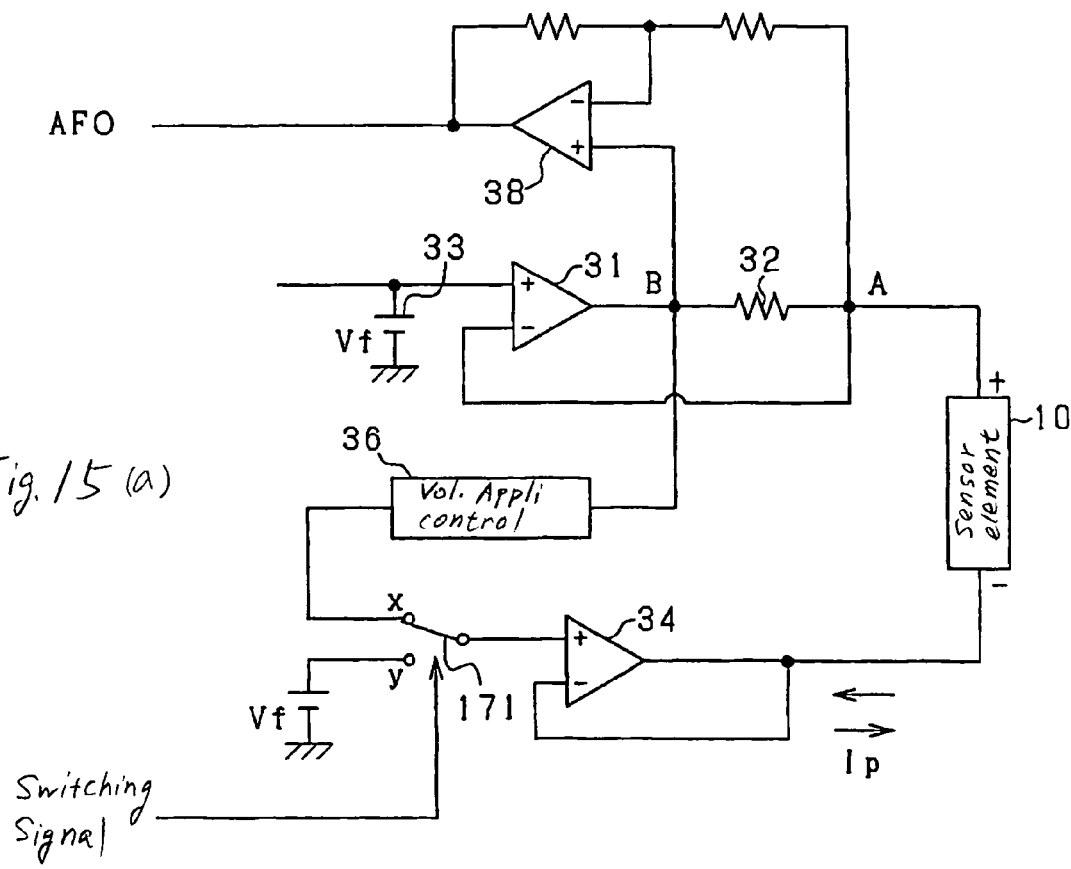
FIG. 15(a) is a circuit diagram which shows a fourth modification of a sensor control circuit.
FIG. 15(b) is a circuit diagram which shows a fifth modification of a sensor control circuit.

FIG. 15(a) shows a modification of the sensor control circuit 30 of FIG. 1 which is designed to place joining terminals leading to the plus and minus terminals of the sensor element 10 at the same electrical potential to establish the virtual stoichiometric AFR measuring mode. Specifically, the switch 171 is disposed between the voltage application control circuit 36 and the operational amplifier 34. The switch 171 is controlled in operation by the switching signal outputted from the microcomputer 20. When the switch 171 establishes a connection between a contact y and the operational amplifier 34, it causes the joining terminals leading to the plus and minus terminals of the sensor element 10 to be placed at the same potential (i.e., the reference voltage Vf), so that 0V is applied to the sensor element 10. This causes the sensor control circuit 30 to be placed in the virtual stoichiometric AFR measuring mode, so that 0 mA flows through the sensor element 10.

Figure 15B:
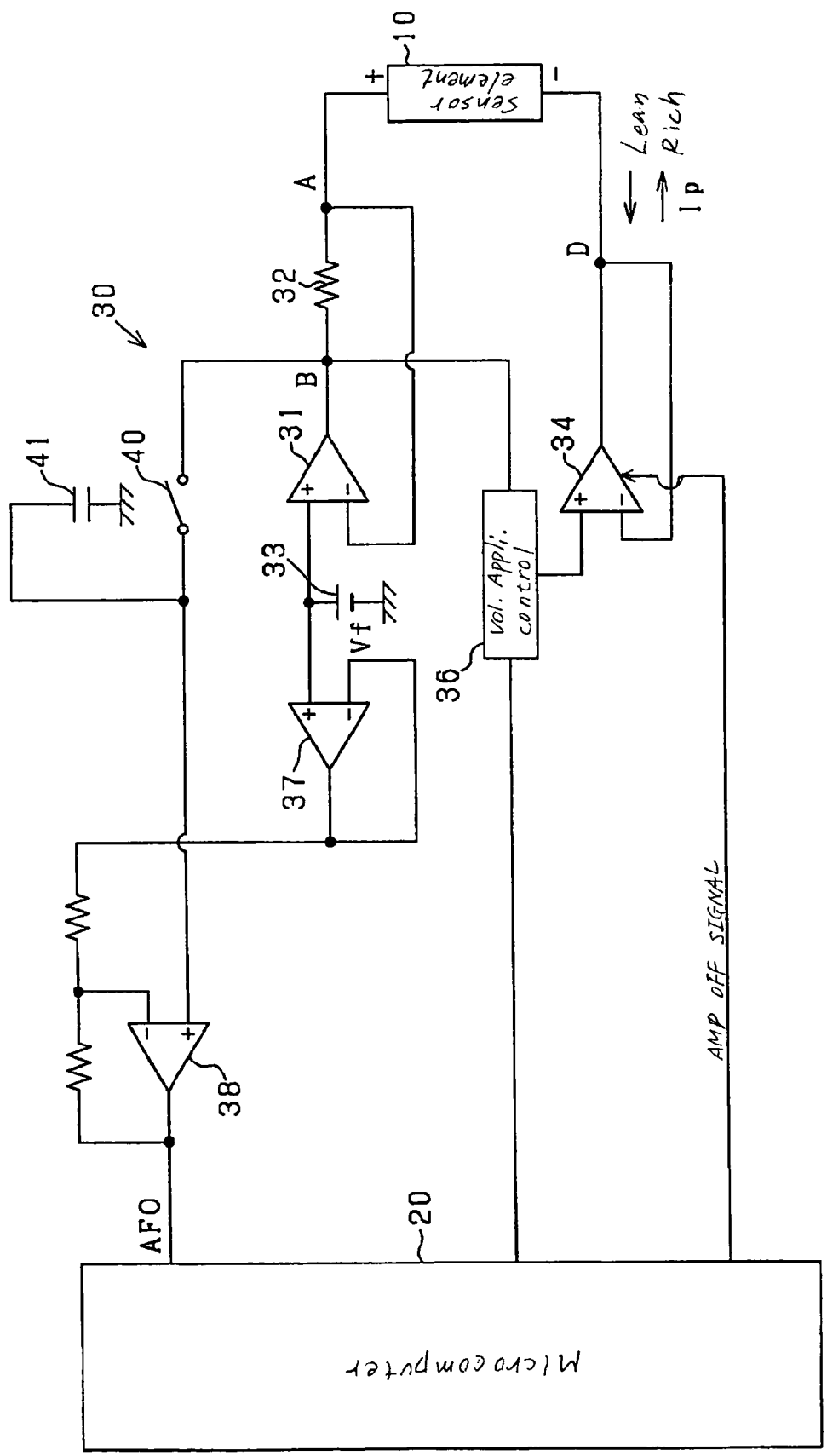

FIG. 15(b) shows another modification of the sensor control circuit 30 of FIG. 1 which is designed to turn off or disenable the operational amplifier 34 to bring the sensor control circuit 30 into the virtual stoichiometric AFR measuring mode. Specifically, when it is required to place the sensor control circuit 30 in the virtual stoichiometric AFR measuring mode, the microcomputer 20 outputs an off-signal to disenable the operation amplifier 34 to inhibit the sensor element current Ip from being produced by the sensor element 10, so that 0 mA flows through the sensor element 10.

The sampling of the offset error K1 may be achieved by bringing the sensor element 10 into a condition where the sensor element 10 produces a reference output other than corresponding to the stoichiometric A/F ratio. In order to minimize the effect of the gain error K2 on an output of the sensor control circuit 30, for example, the reference output is preferably defined as close to a value indicating the stoichiometric A/F ratio as possible.

The determination of the gain error K2 may alternatively be made by detecting the event that the exhaust gas is in an atmosphere other than corresponding to surrounding air in which an output of the A/F sensor is known and sampling an instantaneous value of the A/F output voltage AFO in that atmosphere. This is true for the other sensor control circuits, as described above.

When the sensor control circuit 30 experiences a temperature change, it usually causes the resistance value of the sensor control circuit 30 to change, thus resulting in an error of an output thereof. In order to eliminate such a temperature-dependent error, the microcomputer 20 may be designed to measure the temperature of the sensor control circuit 30 directly or determine it indirectly and calculate and store the offset error K1 on a temperature range basis cyclically. Similarly, the gain error K2 may also be determined on the temperature range basis.

For instance, when the vehicle is running on an uphill road, the throttle is usually kept opened, thus resulting in an increase in temperature of an ECU installed in the vehicle. Therefore, when the throttle continues to be opened for a given period of time, the microcomputer 20 may decide in step 101 of FIG. 5 that the learning time has been reached and determine an error of an output of the sensor control circuit 30, e.g., performing steps 102 to 105 of FIG. 5. Basically, the microcomputer 20 may monitor a change in temperature of the sensor control circuit 30 and determine the offset error K1 and/or the gain error K2 when detecting a temperature change greater than a stated value.

The microcomputer 20 may also be designed to determine an error of an output of the sensor control circuit 30 at least immediately after start-up of the engine or after stop of the engine. For instance, the microcomputer 20 may perform steps 102 to 105, as shown in FIG. 5, 0.5 minutes after the ignition switch of the vehicle is turned on. Alternatively a shut down of the microcomputer 20 may be delayed after the engine is stopped to find the offset error K1 and/or the gain error K2.

The microcomputer 20, as referred to the above embodiments, works to bring the sensor control circuit 30 into a condition equivalent to when the exhaust gas of the engine is stoichiometric and sample an instantaneous value of the A/F output voltage AFO required to compute the offset error K1 and/or, when the exhaust gas is extremely lean or in the atmospheric state during a fuel cut of the engine, sample an instantaneous value of the A/F output voltage AFO required to determine the gain error K2 for correcting the A/F output voltage AFO, but however, it may alternatively be designed to sample the A/F output voltage AFO required to derive the offset error K1 when it is determined that the A/F sensor (i.e., the sensor element 10) is not yet placed in an activated condition. In other words, the microcomputer 20 may work to sample values of the A/F output voltage AFO in two different gas atmospheres to determine two types of errors (i.e., the offset error K1 and the gain error K2) based on reference values of the A/F output voltage AFO known as being correct ones in those two different gas atmospheres for correcting an input of the sensor control circuit 30 indicative of the concentration of a measurement gas (i.e., the A/F output voltage AFO) to the microcomputer 20. Use of the event that the A/F sensor is still in a non-activated condition as a requirement to find the offset error K1 will cause the microcomputer 20 to be subjected to a time restraint needed to sample a value of the A/F output voltage AFO required to determine the offset error K1. However, once the offset error K1 is attained at the start-up of the engine, for example, it makes it possible subsequently to correct the A/F output voltage AFO correctly each time the gain error K2 is found.

Figure 17:
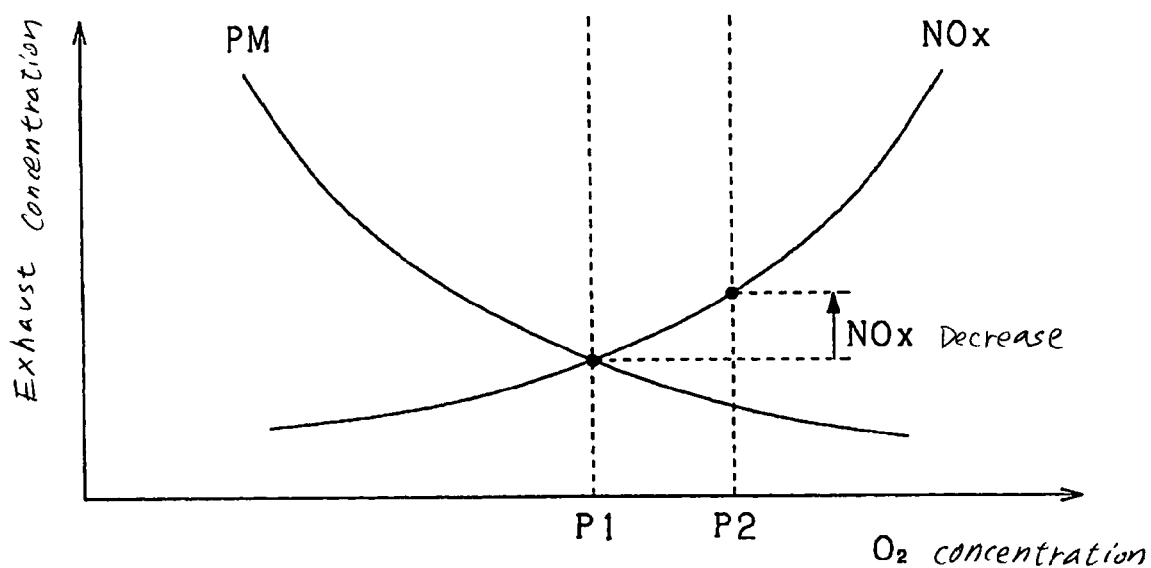
FIG. 17 is a graph which shows distributions of particulates and NOx emitted from a diesel engine in terms of the concentration of oxygen in exhaust emissions of the engine.

Typical diesel engines are required to reduce particulates (PM) or oxides of nitrogen (NOx) contained in exhaust emissions. The concentrations of PM and NOx have relations, as demonstrated in FIG. 17, to the concentration of oxygen ($O_2$) contained in the exhaust emissions. The graph shows that keeping the concentration of $O_2$ at a point P1 (e.g., 10%) enables both the concentrations of PM and NOx to be maintained at a lower level. However, if the concentration of $O_2$ is shifted to a point P2 due to an error of an output of the sensor control circuit, it will result in a greatly decreased efficiency of purifying NOx. The gas concentration measuring apparatus, as described in the above embodiments, is effective to compensate for such an error to maintain the concentration of $O_2$ at the point P1, thereby reducing pollutant emissions of PM and NOx.

Figure 18:
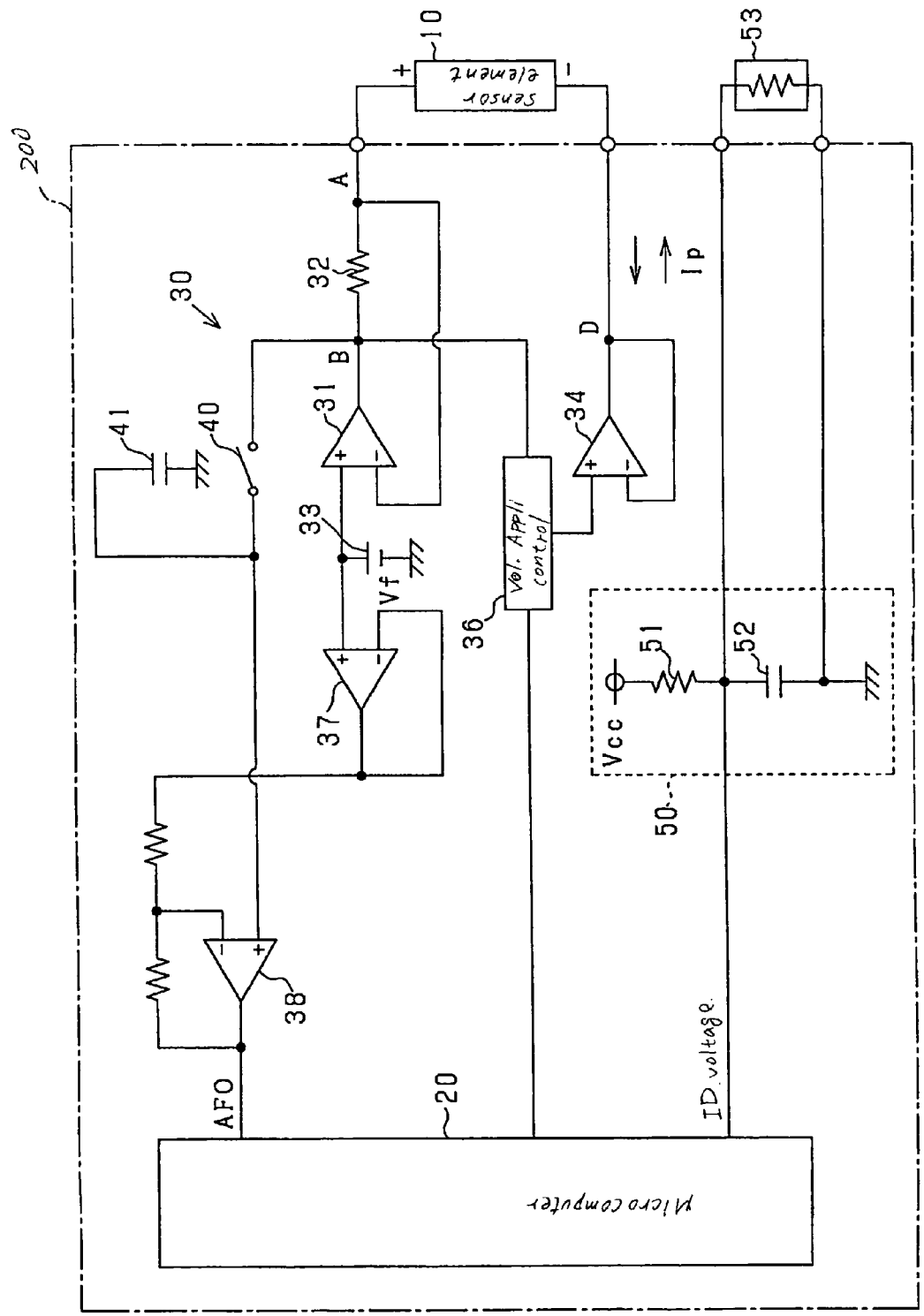
FIG. 18 is a circuit diagram which shows an electric structure of a gas concentration measuring apparatus according to the fourth embodiment of the invention.

FIG. 18 shows a gas concentration measuring apparatus according to the fourth embodiment of the invention which is implemented by an electronic control unit (ECU) 200 installed in the vehicle. The same reference numbers as employed in FIG. 1 refer to the same parts, and explanation thereof in detail will be omitted here.

Usually, the A/F sensor will experience a change in output characteristics (i.e., a change in proportionality to the A/F ratio) due to individual variability or deterioration thereof with time, thereby resulting in a decrease in accuracy of output of the A/F sensor. The output error of the A/F sensor arising from the change in output characteristics usually changes between when the A/F ratio is on the rich side and when it is on the lean side. This is for the following reasons. The output characteristics of the A/F sensor depend upon a gas diffusion rate provided by the diffusion resistance layer 12 of the sensor element 10. When the exhaust gas is lean, it contains excess oxygen, so that the oxygen diffuses, while when it is rich, HC, CO, and H2 that are unburned components of an air-fuel mixture diffuse. The velocity of diffusion is different between molecules of the oxygen and those of the unburned components, which leads to a difference in the output characteristics of the A/F sensor between when the exhaust gas is rich and when it is lean. Note that the output error of the A/F sensor, as referred to in this embodiment, corresponds to the gain error, as referred to in the previous embodiments.

In order to eliminate the above drawback, the ECU 200 of this embodiment is designed to determine a correction factor used in compensating for an error of the A/F output voltage AFO independently when the exhaust gas is rich and when it is lean.

Additionally, the velocity of diffusion of the molecules of oxygen when the exhaust gas is lean and that of the unburned components when the exhaust gas is rich depend upon the gas permeability (i.e., porosity) of the diffusion resistance layer 12. Consequently, a change in the gas permeability arising from the individual variability or deterioration of the A/F sensor will result in a change in the velocity of molecule diffusion, thus causing the error of output of the A/F sensor to change. For instance, if micro cracks occur in the diffusion resistance layer 12 due to the aging of the A/F sensor, it will result in an increase in porosity of the diffusion resistance layer 12. Conversely, if the diffusion resistance layer 12 is clogged, it will result in a decrease in porosity of the diffusion resistance layer 12. This leads to a change in the output characteristics of the A/F sensor.

Figure 19:
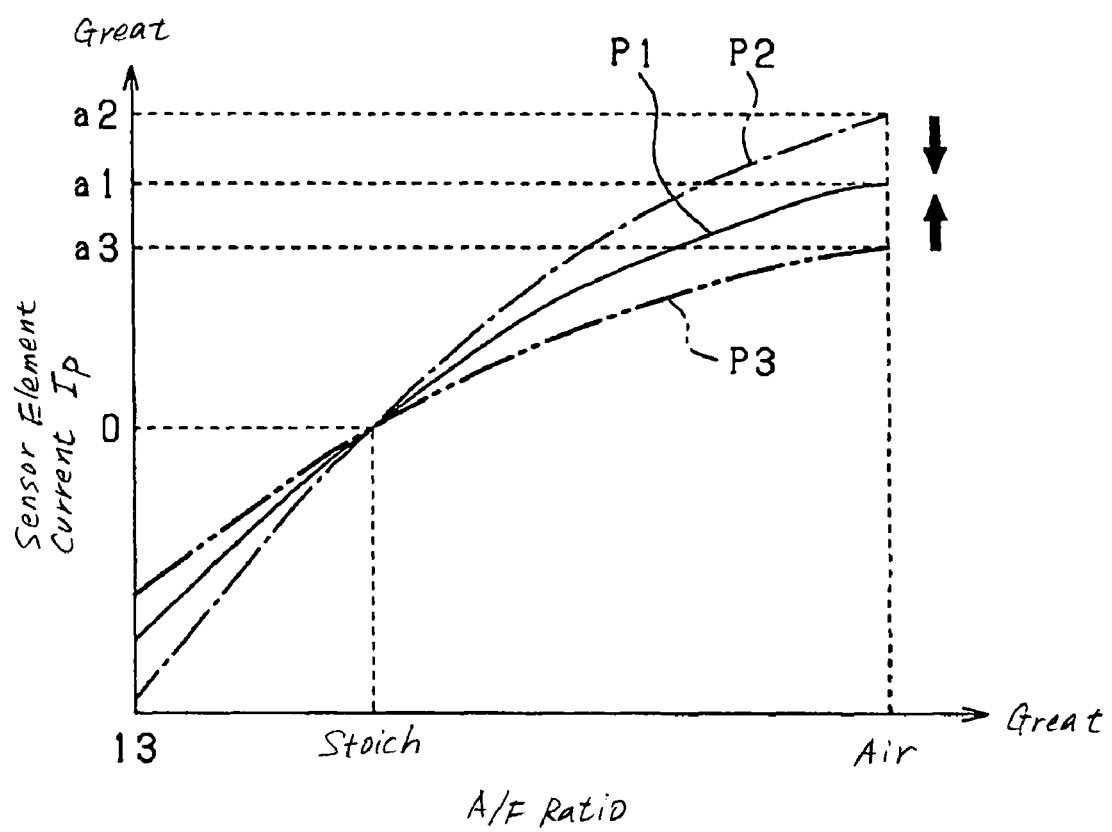
FIG. 19 is a graph which shows distributions of errors of a sensor element current produced by an A/F sensor in terms of an air-fuel ratio.

FIG. 19 demonstrate an example of the output characteristics of the A/F sensor. The abscissa axis indicates the A/F ratio of a mixture supplied to the engine. The ordinate axis indicates the sensor element current Ip produced in the sensor element 10. A solid line P1 represents a reference output characteristic curve. A one-dot chain line P2 represents an output characteristic curve which includes an output error arising from the increase in porosity of the diffusion resistance layer 12 due to the formation of micro cracks. A two-dot chain line P3 represents an output characteristic curve which includes an output error arising from the decrease in porosity of the diffusion resistance layer 12 due to the clogging thereof. When the A/F ratio is equivalent to atmospheric air, the reference output characteristic curve P1 shows Ip=a1. The output characteristic curve P2 shows Ip=a2. The output characteristic curve P3 shows Ip=a3.

Figure 20:
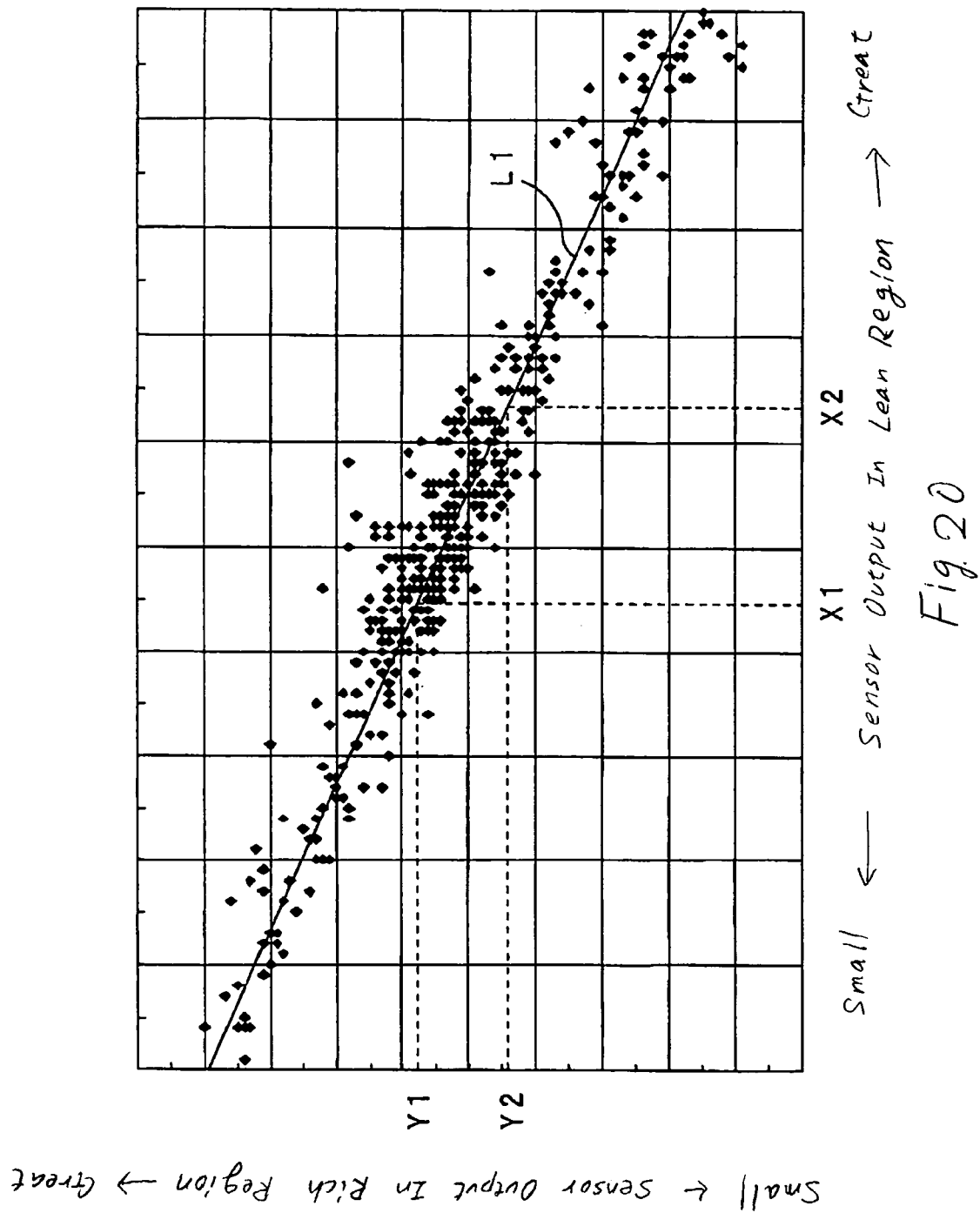
FIG. 20 is a graph which shows a distribution of measured outputs of a plurality of A/F sensors.

FIG. 20 shows a graph demonstrating measured data on output characteristics of a plurality of A/F sensors. Dots represent sampled outputs of the A/F sensors, respectively. The abscissa axis indicates current outputs of the A/F sensors when the exhaust gas is lean (i.e., A/F ratio=18). The ordinate axis indicates current outputs of the A/F sensors when the exhaust gas is rich (e.g., A/F ratio=13). The graph shows that most the sampled outputs of the A/F sensors exist along the line L1 and that the line L1 may be used to specify relations in the current outputs of the A/F sensors between the rich and lean regions.

Considering one of the A/F sensors in FIG. 20 which has actual outputs X2 and Y2 in the lean and rich regions on the line L1 arising from a change in the output characteristics, it is found that the output X2 is X2/X1 times a reference output X1 in the lean region and its reciprocal may be defined as a lean side correction factor $\beta$ (=X1/X2) and that the output Y1 is Y2/Y1 times a reference output Y1 in the rich region and its reciprocal may be defined as a rich side correction factor $\alpha$ (=Y1/Y2).

In a specific example, when X1=0.500 mA, and X2=0.525 mA, the lean side correction factor $\alpha$ is 0.95238. When Y1=−0.399 mA, and Y2=−0.417 mA, the rich side correction factor $\beta$ is 0.95683.

The microcomputer 20 has stored in a memory (e.g., a backup RAM) a map which lists possible combinations of values of the lean and rich side correction factors $\alpha$ and $\beta$ useful for compensating for a change in the output characteristics of the A/F sensor actually employed in the gas concentration measuring apparatus. FIG. 21 demonstrates an example of mapped data on the lean and rich side correction factors $\alpha$ and $\beta$. In this table, 23 different combinations of the lean and rich side correction factors $\alpha$ and $\beta$ are listed according to identification numbers 1 to 23. Each of the combinations of the identification numbers 1 to 11 operates to increase a value of the A/F output voltage AFO, while each of the combinations of the identification numbers 13 to 23 operates to decrease a value of the A/F output voltage AFO to compensate for a change in the output characteristics of the A/F sensor. Each of the lean and rich side correction factors $\alpha$ and $\beta$ to which the identification number 12 is assigned is one (1) which is to be selected when it is determined that there is no change in the output characteristics of the A/F sensor.

Referring back to FIG. 18, the ECU 200 includes an identification voltage generator 50 which works to output an identification signal in the form of voltage to the microcomputer 20. The identification voltage generator 50 is made up of a constant voltage source (Vcc=5V), a reference resistor 51, and a noise removing capacitor 52 which are connected in series. The capacitor 52 connects at ends thereof with an identification resistor 53 through terminals of the ECU 200. The identification resistor 53 has a resistance value which is preselected to compensate for a change in the output characteristics inherent in the A/F sensor used in the gas concentration measuring apparatus and is installed in, for example, a sensor connector. It is advisable that the resistance value of the identification resistor 53 be so selected as to eliminate a change in the output characteristics of the A/F sensor, as measured during a manufacturing process thereof. The reference resistor 51 has a fixed resistance value, as listed as a reference resistance in the map table of FIG. 21. The identification resistor 53 has a resistance value which is different between the identification numbers (i.e., the lean and rich side correction factors $\alpha$ and $\beta$) and listed as an identification resistance in the map table of FIG. 21.

The microcomputer 20 samples the identification voltage, as produced by the identification voltage generator 50, through an A/D port and selects one of the lean and rich side correction factors $\alpha$ and $\beta$ matching a sampled value of the identification voltage by looking up the map table of FIG. 21.

Figure 22:
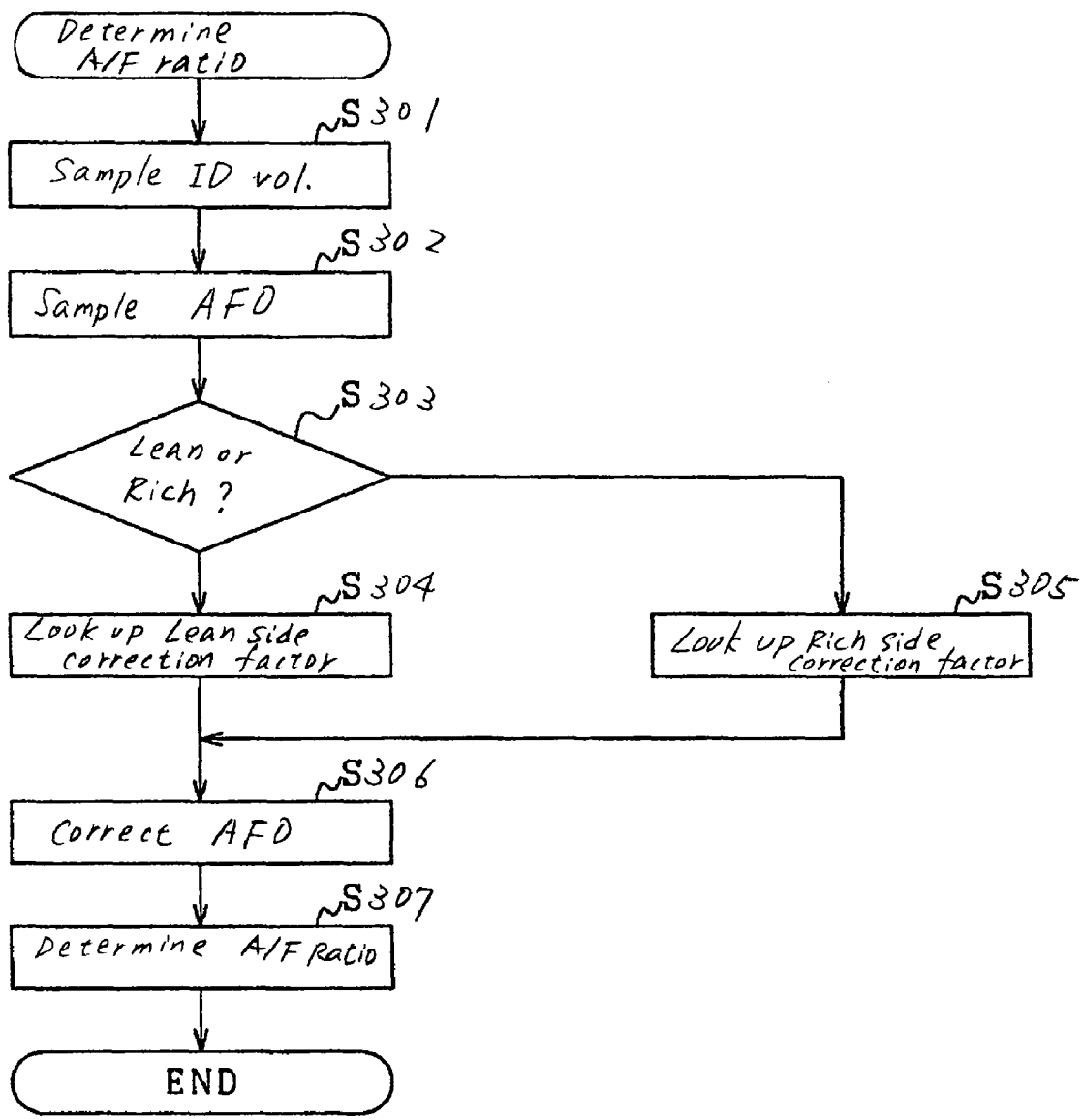
FIG. 22 is a flowchart of a program to be executed by the gas concentration measuring apparatus of FIG. 18 to search lean and rich side correction factors by look-up using the map table of FIG. 21.

FIG. 22 is a flowchart of a program to determine an A/F ratio of a mixture supplied to the engine. The program is executed by the microcomputer 20 in a cycle of, for example, 4 msec.

After entering the program, the routine proceeds to step 301 wherein the identification voltage, as produced by the identification voltage generator 50, is sampled and converted into a digital value. The routine proceeds to step 302 wherein the A/F output voltage AFO is sampled and converted into a digital value. The routine proceeds to step 303 wherein it is determined whether the value of the A/F output voltage AFO is analyzed to determine whether the exhaust gas is lean or rich. If the exhaust gas is determined to be lean, then the routine proceeds to step 304 wherein one of the lean side correction factors $\alpha$ matching the value of the identification voltage, as sampled in step 301, is selected from the map table of FIG. 21. Alternatively, if the exhaust gas is determined to be rich, then the routine proceeds to step 305 wherein one of the rich side correction factors $\beta$ matching the value of the identification voltage, as sampled in step 301, is selected from the map table of FIG. 21.

After step 103 or 105, the routine proceeds to step 306 wherein the value of the A/F output voltage AFO, as sampled in step 320, is corrected using the correction factor $\alpha$ or $\beta$, as searched from the map table of FIG. 22 to compensate for a change in the output characteristics of the A/F sensor. Finally, the routine proceeds to step 307 wherein an A/F ratio of a mixture supplied to the engine is calculated based on the corrected value of the A/F output voltage AFO.

The gas concentration measuring apparatus of this embodiment is, as apparent from the above discussion, designed to ensure compensation for a change in the output characteristics of the A/F sensor usually different between when the exhaust gas is rich and when it is lean, thereby enabling the A/F ratio to be determined with high accuracy either in the rich or lean region. This provides a wide range feedback control of the A/F ratio cover the rich to lean region. For instance, when rich feedback control is being performed in response to an acceleration demand in order to protect the engine or improve fuel consumption in the engine, the gas concentration measuring apparatus of this embodiment is very useful for such a purpose.

The gas concentration measuring apparatus of the fifth embodiment will be described below.

Usually, the output characteristics of the A/F sensor experience a change with aging thereof. In order to compensate for such a change, the microcomputer 20 first works to find a change in the output characteristics of the A/F sensor when the exhaust gas is in an atmospheric state, that is, when surrounding air whose concentration of oxygen is known is sucked into the engine and determine or update the lean or rich side correction factor $\alpha$ or $\beta$ for use in correcting the A/F output voltage AFO. Specifically, the microcomputer 20 samples a value of the A/F output voltage AFO when the exhaust gas is in the atmospheric state to determine an error of the A/F output voltage AFO in the lean region and also determines an error of the A/F output voltage AFO in the rich region using the one in the lean region. The microcomputer 20 then determines the lean and rich side correction factors using the determined errors and correct the value of the A/F output voltage AFO using one of the lean and rich side correction factors.

The gas concentration measuring apparatus of this embodiment has the same structure as the ECU 200 in FIG. 18, but may alternatively not include the identification voltage generator 50.

Figure 23:
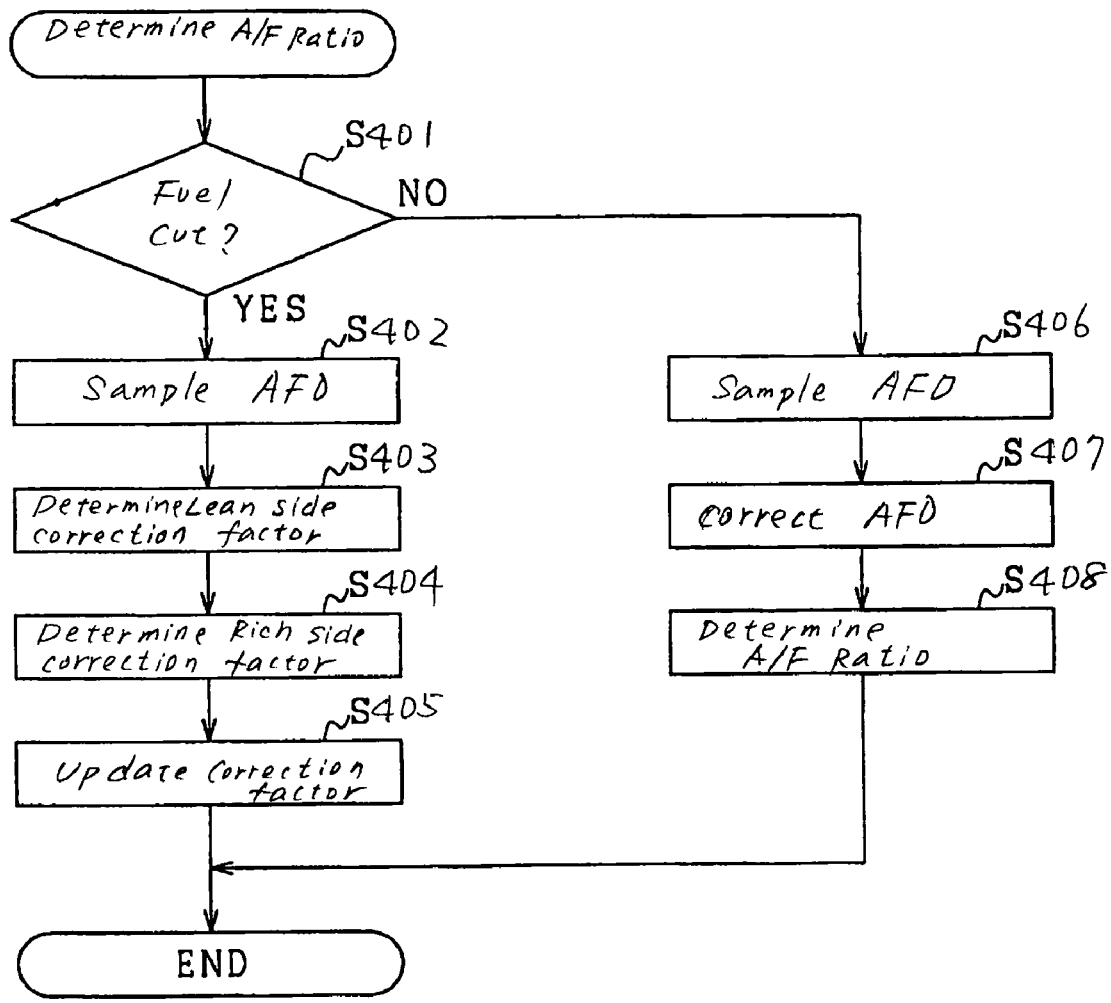
FIG. 23 is a flowchart of a program to be executed by a gas concentration measuring apparatus of the fifth embodiment of the invention to calculate lean and rich side correction factors mathematically.

FIG. 23 is a flowchart of a program to be executed by the microcomputer 20 cyclically at a stated time interval to determine an A/F ratio of a mixture supplied to the engine.

After entering the program, the routine proceeds to step 401 wherein it is determined whether the engine is now undergoing a fuel cut or not. If a YES answer is obtained, it means that an air-fuel mixture is not burned in a combustion chamber of the engine, so that the sensing element 10 senses an atmospheric gas and produces an output indicating the concentration of oxygen in the atmospheric gas. The routine then proceeds to step 407 wherein an instantaneous value of the A/F output voltage AFO is sampled. The routine proceeds to step 403 wherein a lean side correction factor is determined according to a relation below.

lean side correction factor=$(Vair-2.2V)/(AFO-2.2V)$ where Vair is a reference voltage that is a correct level of the A/F output voltage AFO to be attained when the exhaust gas is in the atmospheric state.

The routine proceeds to step 204 wherein an output characteristic curve predefined by mapping relations between outputs of the sensor element 10 when the exhaust gas is in the atmospheric state and those when the exhaust gas is in the rich region is looked up to search an output of the sensor element 10 (i.e., the sensor element current Ip) in the rich region which matches the value of the A/F output voltage AFO, as sampled in step 402. Note that the output characteristic curve may be prepared by defining the abscissa axis of the graph in FIG. 20 as representing outputs of the A/F sensor when the exhaust gas in the atmospheric state. Next, a rich side correction factor is determined using the searched output and a corresponding rich side reference output. For example, using the map table of FIG. 20 in which the abscissa axis is altered to represent the outputs of the A/F sensor when the exhaust gas in the atmospheric state, the output Y2 of the A/F sensor in the rich region is searched which matches the value of the A/F output voltage AFO, as sampled in step 402. The rich side correction factor is calculated by dividing the reference output Y1 in the rich region by the output Y2 (i.e., Y1/Y2). Finally, the routine proceeds to step 405 wherein the lean and rich side correction factors, as stored in a memory of the microcomputer 20 are updated to those, as determined in steps 403 and 404.

If a NO answer is obtained in step 401 meaning that the engine is not undergoing a fuel cut, then the routine proceeds to step 406 wherein a value of the A/F output voltage AFO is sampled. The routine proceeds to step 407 wherein the value of the A/F output voltage AFO, as sampled in step 406, is corrected using the lean or rich side correction factor as stored in the memory. Specifically, when the value of the A/F output voltage AFO represents the fact that the A/F ratio is lean (i.e., a lean mixture), the value of the A/F output voltage AFO, as sampled in step 406, is corrected using the lean side correction factor. Alternatively, when the value of the A/F output voltage AFO represents the fact that the A/F ratio is rich (i.e., a rich mixture), the value of the A/F output voltage AFO, as sampled in step 406, is corrected using the rich side correction factor.

Finally, the routine proceeds to step 408 wherein an A/F ratio is calculated using the corrected value of the A/F output voltage AFO.

The gas concentration measuring apparatus of this embodiment, as apparent from the above discussion, serves to correct the value of the A/F output voltage AFO so as to compensate for a change in the output characteristics of the A/F sensor arising from the aging thereof.

The gas concentration measuring apparatus of the fourth embodiment, as already described with reference to FIG. 20, has installed in the ECU 200 the identification voltage generator 50 which works to output the identification signal to the microcomputer 20 for searching the lean or rich side correction factor by look-up using the map table of FIG. 21, but however, it may alternatively be designed to receive the identification signal outputted directly from an external without through the identification voltage generator 50.

The gas concentration measuring apparatus of the fifth embodiment, as described above, works to search and update the lean and rich side correction factors when the exhaust gas is placed in a reference gas atmosphere that is a surrounding air atmosphere, but may alternatively be designed to define a given lean atmosphere of the exhaust gas other than the surrounding air atmosphere in which the concentration of a specific gas component (e.g., oxygen) is known, sample an actual output of the A/F sensor when the exhaust gas reaches the reference gas atmosphere to estimate an output of the A/F sensor when the exhaust gas is in a corresponding rich state by look-up using a predefined lean-to-rich relation, and determine the lean and rich side correction factors based on the sampled and estimated outputs of the A/F sensor and corresponding reference outputs.

The gas concentration measuring apparatuses of the fourth and fifth embodiments may also employ the sensor element 60, as illustrated in FIG. 9, or the sensor element 100, as illustrated in FIG. 12.

The gas concentration measuring apparatus, as described in each of the above fourth and fifth embodiments, may be used with a composite gas concentration measuring sensor which includes first and second cells made of a solid electrolyte body. The first cell works as a pump cell to pump oxygen molecules out of or into a first gas chamber formed in a sensor body and output a signal indicative of the concentration of the pumped oxygen molecules. The second cell works as a sensor cell to produce a signal indicative of the concentration of a preselected component of gasses flowing into a second gas chamber from the first gas chamber. For example, the composite gas concentration measuring sensor may be used to measure the concentration NOx contained in exhaust gasses of the automotive engine. Further, the composite gas concentration measuring sensor may be designed to have a third cell serving as a monitor cell or a second pump cell to produce an electromotive force as a function of concentration of oxygen molecules remaining in the second gas chamber.

The gas concentration measuring apparatus may alternatively be designed to measure the concentration of HC or CO contained in the exhaust gasses of the automotive engine. The measurement of concentration of HC or CO is achieved by pumping excessive oxygen ($O_2$) out of the first gas chamber using the pump cell and decomposing HC or CO contained in the gasses entering the second gas chamber using the sensor cell to produce an electric signal indicative of the concentration of HC or CO.

The gas concentration measuring apparatus in each of the above embodiment may alternatively be employed to measure the concentration of a gas other than a preselected component contained in exhaust emissions of automotive engines.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas concentration measuring apparatus comprising:
a gas concentration sensor which includes a solid electrolyte body to be exposed to an exhaust gas within an exhaust system of an internal combustion engine;
a sensor control circuit which works to control an operation of said gas concentration sensor and operate in a gas measuring mode and a reference output mode selectively, in the gas measuring mode, said sensor control circuit applying a voltage to said gas concentration sensor and sampling a resulting flow of electric current through said gas concentration sensor to produce a gas concentration output as a function of a concentration of a given component of the exhaust gas, in the reference output mode, said sensor control circuit being placed in a condition which is equivalent to when the exhaust gas is in a preselected atmosphere and in which a reference output is produced insensitive to the exhaust gas;
a switching circuit working to switch a mode of operation of said sensor control circuit from the gas measuring mode to the reference output mode; and
a correcting circuit working to sample a value of the reference output as produced by said sensor control circuit being placed in the reference output mode and find an error of the gas concentration output of said sensor control circuit as a function of a difference between the sampled value of the reference output and a corresponding normal reference output as expected to be attained by said sensor control circuit correctly when the exhaust gas is in the preselected atmosphere to determine a correction factor, said correcting circuit correcting the gas concentration output of said sensor control circuit using the correction factor so as to compensate for the error;
wherein the reference output mode is established by placing said sensor control circuit in a virtual stoichiometric air-fuel ratio measuring mode equivalent to an operation mode in which said sensor control circuit produces the gas concentration output when the exhaust gas results from burning of a stoichiometric mixture in the engine; and
said switching circuit switches the mode of operation of said sensor control circuit from the gas measuring mode to the reference output mode at a stated time interval.

2. A gas concentration measuring apparatus as set forth in claim 1, wherein said switching circuit includes a switch installed in a current flow line of said sensor control circuit which connects with said gas concentration sensor, and wherein said switching circuit works to open the switch to place said sensor control circuit in the virtual stoichiometric air-fuel ratio measuring mode.

3. A gas concentration measuring apparatus as set forth in claim 1, wherein said switching circuit includes a switch connecting between an output of an amplifier and said gas concentration sensor, and wherein said switching circuit works to open the switch to place said sensor control circuit in the virtual stoichiometric air-fuel ratio measuring mode.

4. A gas concentration measuring apparatus as set forth in claim 1, wherein said sensor control circuit includes a current-measuring resistor and a switch, said current-measuring resistor being connected to one of a positive and a negative terminal of said gas concentration sensor so that the electric current resulting from application of the voltage to said gas concentration sensor flows through said current-measuring resistor, said switch being installed in a current flow line of said sensor control circuit leading to the other of the positive and negative terminals of said gas concentration sensor, and wherein said switching circuit works to open the switch to place said sensor control circuit in the virtual stoichiometric air-fuel ratio measuring mode.

5. A gas concentration measuring apparatus as set forth in claim 1, wherein said switching circuit works to place a positive and a negative terminal of said gas concentration sensor at the same potential to bring said sensor control circuit into the virtual stoichiometric air-fuel ratio measuring mode.

6. A gas concentration measuring apparatus as set forth in claim 1, wherein said switching circuit switches the mode of operation of said sensor control circuit from the gas measuring mode to the reference output mode when a control system for the internal combustion engine is in a condition not to require the gas concentration output of said sensor control circuit.

7. A gas concentration measuring apparatus as set forth in claim 1, wherein said switching circuit switches the mode of operation of said sensor control circuit from the gas measuring mode to the reference output mode when said sensor control circuit experiences a change in temperature thereof.

8. A gas concentration measuring apparatus as set forth in claim 1, wherein:
said switching circuit switches the mode of operation of said sensor control circuit from the gas measuring mode to the reference output mode at least immediately after start-up of the engine or when the engine is stopped; and
said correcting circuit determines the correction factor cyclically to update a value of the correction factor, said correcting circuit storing the updated correction factor.

9. A gas concentration measuring apparatus as set forth in claim 8, wherein said correcting circuit stores the updated correction factor on a basis of temperature of said sensor control circuit.

10. A gas concentration measuring apparatus as set forth in claim 1, wherein said correcting circuit also works to sample a value of the gas concentration output which is produced by said sensor control circuit placed in the gas measuring mode when the exhaust gas is in a given reference atmosphere that is different from an atmosphere of the exhaust gas equivalent to when said sensor control circuit produces a value of the gas concentration output identical with the reference output, said correcting circuit finding a second error of the gas concentration output of said sensor control circuit as a function a difference between the sampled value of the gas concentration output and a corresponding normal reference output as expected to be attained by said sensor control circuit correctly when the exhaust gas is in the given reference atmosphere, and wherein said correcting circuit determines the correction factor using the second error and a first error that is the error, as found as a function of the difference between the sampled value of the reference output and the corresponding normal reference output, and corrects the gas concentration output of said sensor control circuit using the correction factor so as to compensate for the first and second errors.

11. A gas concentration measuring apparatus as set forth in claim 10, wherein said given reference atmosphere is an atmosphere of the exhaust gas resulting from burning of a mixture equivalent to surrounding air.

12. A gas concentration measuring apparatus as set forth in claim 1, wherein said correcting circuit also works to sample a value of the gas concentration output which is produced by said sensor control circuit placed in the gas measuring mode when the exhaust gas is in a given reference atmosphere that is different from an atmosphere of the exhaust gas equivalent to when said sensor control circuit produces a value of the gas concentration output identical with the reference output, said correcting circuit finding a second error of the gas concentration output of said sensor control circuit as a function a difference between the sampled value of the gas concentration output and a corresponding normal reference output as expected to be attained by said sensor control circuit correctly when the exhaust gas is in the given reference atmosphere, and further comprising a rich/lean decision circuit which works to decide whether the exhaust gas is in a rich state or a lean state, said correcting circuit working to determine one of a rich side correction factor and a lean side correction factor which matches one of the rich and lean states, as decided by said rich/lean decision circuit, and is required to compensate for the second error, said correcting circuit correcting the gas concentration output of said sensor control circuit using the one of the rich and lean side correction factor.

13. A gas concentration measuring apparatus as set forth in claim 1, wherein said switching circuit is designed to produce a current output inhibit signal which inhibits said gas concentration sensor from producing the electric current to bring said sensor control circuit into the virtual stoichiometric air-fuel ratio measuring mode.

14. A gas concentration measuring apparatus as set forth in claim 1, wherein said sensor control circuit includes an amplifier through which the voltage is applied to said gas concentration sensor in the gas measuring mode, and wherein said switching circuit works to output an off-signal to disenable the amplifier to bring said sensor control circuit into the virtual stoichiometric air-fuel ratio measuring mode.

* * * * *